(12) United States Patent
Spenciner et al.

(10) Patent No.: US 11,911,084 B2
(45) Date of Patent: Feb. 27, 2024

(54) METHOD FOR USING SCAPULAR TETHERS

(71) Applicant: Medos International Sarl, Le Locle (CH)

(72) Inventors: David B. Spenciner, North Attleboro, MA (US); Stefan Gabriel, Mattapoisett, MA (US); Mehmet Ziya Sengun, Canton, MA (US); Donald E. Barry, Norwood, MA (US); Philipp Moroder, Berlin (DE); Marc Jacofsky, Phoenix, AZ (US); Aaron Chamberlain, St. Louis, MO (US); Annemarie Bridgette von Rechenberg, Birmensdorf (CH); John M. Tokish, Scottsdale, AZ (US); Brianna Lee, Portsmouth, RI (US); Gary McAlister, Franklin, MA (US); Benjamin Cleveland, Weymouth, MA (US)

(73) Assignee: Medos International Sarl, Le Locle (CH)

( * ) Notice: Subject to any disclaimer, the term of this patent is extended or adjusted under 35 U.S.C. 154(b) by 405 days.

(21) Appl. No.: 17/147,114

(22) Filed: Jan. 12, 2021

(65) Prior Publication Data

US 2022/0218399 A1    Jul. 14, 2022

(51) Int. Cl.
*A61F 2/08* (2006.01)
*A61B 17/84* (2006.01)
(Continued)

(52) U.S. Cl.
CPC .............. *A61B 17/842* (2013.01); *A61F 2/40* (2013.01); *A61B 2017/00862* (2013.01);
(Continued)

(58) Field of Classification Search
CPC ........ A61B 17/482; A61F 2/08; A61F 2/0811; A61F 2/40; A61F 2/68; B25J 9/1075
See application file for complete search history.

(56) References Cited

U.S. PATENT DOCUMENTS

| 4,735,196 A | 4/1988 | Krag et al. |
| 5,070,865 A | 12/1991 | Iams |

(Continued)

FOREIGN PATENT DOCUMENTS

| CN | 104306059 B | 9/2016 |
| EP | 2736362 B1 | 10/2017 |

(Continued)

OTHER PUBLICATIONS

Extended European Search Report for EP Pat. App. No. 22151032.4 dated Oct. 6, 2022.

(Continued)

*Primary Examiner* — Marcia L Watkins

(57) ABSTRACT

In general, scapular tethers and methods of using scapular tethers are provided. A tether is configured to be implanted in a body of a patient and to control movement of the patient's scapula. In an exemplary embodiment, the tether is configured to be attached to at least one body structure in a patient. The tether includes a flexible member configured to, when implanted in the patient, flex in response to movement of the patient's scapula accompanying arm movement of the patient.

13 Claims, 17 Drawing Sheets

(51) Int. Cl.
*A61F 2/40* (2006.01)
*A61B 17/00* (2006.01)
*A61F 2/30* (2006.01)

(52) U.S. Cl.
CPC ....... *A61B 2017/00942* (2013.01); *A61F 2/08* (2013.01); *A61F 2/0811* (2013.01); *A61F 2002/0852* (2013.01); *A61F 2002/30731* (2013.01)

(56) References Cited

U.S. PATENT DOCUMENTS

| | | | |
|---|---|---|---|
| 5,623,948 | A | 4/1997 | Van Morris |
| 5,857,990 | A | 1/1999 | Maas |
| 5,902,261 | A | 5/1999 | Schwartz |
| 5,937,442 | A | 8/1999 | Yamaguchi et al. |
| 6,314,580 | B1 | 11/2001 | Greenberg et al. |
| 6,440,094 | B1 | 8/2002 | Maas |
| 7,547,289 | B2 | 6/2009 | Branch |
| 7,913,323 | B2 | 3/2011 | Takamoto et al. |
| 8,308,668 | B1 | 11/2012 | Harvat |
| 8,894,597 | B2 | 11/2014 | Newkirk |
| 8,905,956 | B2 | 12/2014 | Waeger |
| 8,931,837 | B2 | 1/2015 | Vernon |
| 9,009,863 | B2 | 4/2015 | Decker |
| 9,119,707 | B2 | 9/2015 | Brown |
| 9,913,638 | B2 * | 3/2018 | Saliman ............ A61B 17/0642 |
| 9,931,136 | B2 | 4/2018 | Shenoy et al. |
| 9,962,554 | B2 | 5/2018 | Feng |
| 10,016,297 | B2 | 7/2018 | Bue, Jr. et al. |
| 10,478,327 | B2 | 11/2019 | Liu |
| 10,569,071 | B2 | 2/2020 | Harris et al. |
| 10,582,999 | B2 | 3/2020 | Kovacs |
| 2002/0082537 | A1 | 6/2002 | MacAllister |
| 2005/0143737 | A1 | 6/2005 | Pafford et al. |
| 2006/0047233 | A1 | 3/2006 | Dussaussoy |
| 2008/0208089 | A1 | 8/2008 | Newkirk et al. |
| 2009/0264799 | A1 | 10/2009 | Bonutti et al. |
| 2010/0228171 | A1 | 9/2010 | Waldridge |
| 2011/0264216 | A1 | 10/2011 | Makower et al. |
| 2011/0295284 | A1 * | 12/2011 | Purdue ...................... A61F 2/08 606/151 |
| 2012/0179080 | A1 | 7/2012 | Sakamoto et al. |
| 2014/0163427 | A1 | 6/2014 | Stimson et al. |
| 2014/0276306 | A1 | 9/2014 | Dreske |
| 2015/0148852 | A1 * | 5/2015 | Zhang ................. A61B 17/842 606/328 |
| 2016/0038370 | A1 | 2/2016 | Dreske |
| 2016/0228234 | A1 | 8/2016 | Hansen et al. |
| 2017/0216635 | A1 | 8/2017 | Stibilj |
| 2017/0231793 | A1 | 8/2017 | Parr et al. |
| 2017/0246071 | A1 | 8/2017 | Schultz et al. |
| 2017/0311875 | A1 | 11/2017 | Ludewig et al. |
| 2017/0354530 | A1 | 12/2017 | Shagdar et al. |
| 2018/0256227 | A1 | 9/2018 | Maxson |
| 2018/0271409 | A1 | 9/2018 | Gong et al. |
| 2018/0296318 | A1 | 10/2018 | Wallace et al. |
| 2019/0297959 | A1 | 10/2019 | Liu |
| 2019/0350738 | A1 | 11/2019 | Webster et al. |
| 2019/0365554 | A1 | 12/2019 | Davies-Sekle |
| 2022/0378486 | A1 * | 12/2022 | Holowecky ...... A61B 17/06166 |

FOREIGN PATENT DOCUMENTS

| | | |
|---|---|---|
| JP | 3953762 B2 | 8/2007 |
| JP | 4580807 B2 | 11/2010 |
| JP | 5749713 B2 | 7/2015 |
| JP | 2015525094 A | 9/2015 |
| JP | 5923444 B2 | 5/2016 |
| KR | 101071481 B1 | 10/2011 |
| KR | 101369684 B1 | 3/2014 |
| RU | 2150910 C1 | 6/2000 |
| RU | 2295926 C2 | 3/2007 |
| RU | 2359629 C2 | 6/2009 |
| RU | 2405482 C1 | 12/2010 |
| RU | 2468762 C1 | 12/2012 |
| RU | 2468763 C1 | 12/2012 |
| RU | 2496440 C2 | 10/2013 |
| WO | WO-1995027533 A1 | 10/1995 |
| WO | WO-2019185946 A1 | 10/2019 |

OTHER PUBLICATIONS

"Dynacord™ Suture for Soft Tissue Repair Procedures Value Analysis Brief," Depuy Synthes, 2018.
"Dynacord™ Suture: The Future of Soft Tissue Repair," Depuy Synthes, 2018.
Electronics Tutorials, "Potentiometers," dated no later than Sep. 29, 2018 (available at <https://www.electronics-tutorials.ws/resistor/potentiometer.html>) (19 pages).
Haupt et al. (Jun. 20, 2020), "Biomechanical Properties of Small-Size Hamstring Autografts," Cureus 12(6): e8728. DOI 10.7759/cereus.8728.
Kibler et al., "Current concepts: scapular dyskinesis." Br J Sports Med 2010;44:300-305.
Moroder, "Shoulder-Pacemaker Treatment Concept for Posterior Positional Functional Shoulder Instability: A Prospective Clinical Trial," AJSM 2020.
Scheffler et al., "Biomechanical Comparision of Hamstring and Patellar Tendon Graft Anterior Cruciate Ligament Reconstruction Techniques: The Impact of Fixation Level and Fixation Method Under Cyclic Loading," Arthroscopy: The Journal of Arthroscopic and Related Surgery, vol. 18, No. 3, Mar. 2002, p. 304-315.
Straight et al., "Soft Tissue Fixation to Bone: A Biochemical Analysis of Spiked Washers," The American Journal of Sports Medicine, vol. 22, No. 3, 1994, p. 339-343.
Wu et al., "ISB recommendation on definitions of joint coordinate systems of various joints for the reporting of human joint motion—Part II: shoulder, elbow, wrist and hand." J Biomech 2005;38:981-992.

* cited by examiner

METHOD FOR USING SCAPULAR TETHERS

FIELD

The present disclosure generally relates to scapular tethers.

BACKGROUND

The shoulder joint has the largest range of motion of any joint in the human body. It is a ball-and-socket joint having three bones: a shoulder blade (scapula), a collarbone (clavicle), and an upper arm bone (humerus).

A rounded head of the upper arm bone (humeral head) fits into a shallow socket in the shoulder blade called a glenoid. The humeral head is usually much larger than the glenoid, and together they have little inherent stability. The shoulder joint is thus prone to instability and dislocation. A soft fibrous tissue rim called a labrum surrounds the glenoid to form a cup for the humeral head to move within the glenoid. The labrum thus helps maintain stability of the shoulder, while allowing for a very wide range of motion. When the labrum of the shoulder joint is damaged, the stability of the shoulder joint is compromised, leading to subluxation and dislocation of the joint. Recurrent dislocations may cause damage to the bones of the joint—the humeral head and the glenoid. In particular, damage to the anterior-inferior part of the glenoid will cause a decrease in the area of contact with the humeral head.

Surgical reconstruction targeting the shoulder joint's soft tissues (which typically involves labral repairs) can be adequate to address certain shoulder instability problems. However, in cases where significant bone deficiency is present (e.g., when greater than 20% of the glenoid's surface area is missing), addressing only the soft tissue issues is typically not sufficient. When bone deficiencies reach certain dimensions, reconstruction of these deficits is typically performed using a bone graft. Although existing techniques have been used with some success, the bone graft may not be properly aligned with the glenoid or other bone structure being reconstructed. In particular, when the bone to be reconstructed is being prepared for receiving the graft, it may be challenging to identify proper locations for attachment elements (e.g., screws) that are to be inserted into the bone when the graft is attached thereto.

A rotator cuff at the shoulder helps stabilize the shoulder. The rotator cuff includes four muscles and their tendons: the supraspinatus muscle, the infraspinatus muscle, the teres minor muscle, and the subscapularis muscle. The rotator cuff can become torn (rotator cuff tear), which can cause pain and reduced arm function.

A rotator cuff tear can be partial or complete. In the case of a partial tear, the injury will frequently heal itself, if given sufficient time and if care is taken not to expose the injury to further undue stress. In the case of a complete tear, however, surgery is often needed to reattach the rotator cuff to its associated bone or bones, e.g., the humerus and/or the scapula. Numerous devices are currently available to reattach the rotator cuff to bone. Examples of such currently-available devices include screws, staples, suture anchors, and tacks. While such currently-available devices can be effective in reattaching the rotator cuff to bone, in some cases the rotator cuff tear does not heal completely or the rotator cuff tear recurs after surgery as the patient moves the shoulder in the course of their daily life. The patient therefore may again experience pain and reduced arm function and may require another surgery and/or other treatment to address the torn rotator cuff.

During motions of the arm, motion and positions of the scapula occur along with the motions and position of the humerus. When the motions and positions of the scapula are normal in relation to the motions and position of the humerus, the resulting pattern of relative positions between the glenoid on the scapula and the humeral head correlates with normal function of the arm. Scapular dyskinesis refers to the scapula moving or being positioned abnormally with respect to the thorax. Scapular dyskinesis can cause pain and restricted arm movement and can lead to complications. In less severe cases, scapular dyskinesis can be improved non-surgically, such as with physical therapy, bracing, application of cold to reduce inflammation, and/or other treatments. In more severe cases, e.g., when one or more complications such as constant pain, a torn rotator cuff tear, shoulder stiffness, etc. are present, surgery is often performed to reduce scapular dyskinesis. While surgery can be effective initially, in some cases the scapular dyskinesis recurs after surgery as the patient moves the shoulder in the course of their daily life. In such cases, the patient may again experience pain and reduced arm function and may require another surgery and/or other treatment to treat the scapular dyskinesis.

Accordingly, there remains a need for improved shoulder repair.

SUMMARY

In general, scapular tethers and methods of using scapular tethers are provided.

In one aspect, a surgical system is provided that in one embodiment includes an elongate flexible implant configured to be implanted in a body of a person. The elongate flexible implant includes a first terminal end and a second terminal end. The first terminal end of the elongate flexible implant is configured to attach to a rib of the person. The surgical system also includes a cam configured to be implanted in the body of the person and to be attached to the rib or to a scapula of the person. The second terminal end of the elongate flexible implant is configured to be attached to the scapula of the person. With the first terminal end attached to the rib and the second terminal end attached to the scapula, the elongate flexible implant is configured to extend along an exterior surface of the cam. With the first terminal end attached to the rib and the second terminal end attached to the scapula, the elongate flexible implant is configured to, in response to movement of the scapula, change in length relative to the rib and the scapula.

The surgical system can vary in any number of ways. For example, the surgical system can include a grommet configured to be attached to the rib or the scapula, and, with the grommet attached to the rib or the scapula, the first terminal end attached to the rib, and the second terminal end attached to the scapula, the elongate flexible implant can be configured to extend through a hole of the grommet. For another example, the first terminal end of the elongate flexible implant can be configured to attach directly to the rib of the person. For yet another example, the cam can be configured to be attached to the scapula, the second terminal end of the elongate flexible implant can be configured to attach indirectly to the scapula of the person with the second terminal end of the elongate flexible implant being attached to the cam, and the cam can be configured to move with the scapula simultaneously with the elongate flexible implant changing in length relative to the rib and the scapula. For still another example, the second terminal end of the elongate flexible implant can be configured to attach directly to the scapula of the person. For yet another example, the cam can be configured to attach to the rib, the surgical system can also include a second cam configured to attach to the scapula, the first terminal end of the elongate flexible implant can be configured to attach indirectly to the scapula of the person via the second cam, and, with the first terminal end attached to the rib and the second terminal end attached to the scapula, the elongate flexible implant can be configured to extend along an exterior surface of the second cam. For still another example, the cam can be configured to attach to the scapula, the cam attached to the scapula can be configured to move with the scapula simultaneously with the elongate flexible implant flexing relative to the rib and the scapula, the surgical system can also include a second cam configured to attach to the rib, the first terminal end of the elongate flexible implant can be configured to attach indirectly to the rib of the person via the second cam, and, with the first terminal end attached to the rib and the second terminal end attached to the scapula, the elongate flexible implant can be configured to extend along an exterior surface of the second cam.

For another example, the cam can be configured to move from a first position, in which the elongate flexible implant has a first length, to a second position, in which the elongate flexible implant has a second length that is greater than the first length, and the movement of the scapula can cause the movement of the cam from the first position to the second position. In some embodiments, the movement of the scapula in a first direction can cause the movement of the cam from the first position to the second position such that the elongate flexible implant increase in length, and the movement of the scapula in a second direction that is opposite to the first direction is configured to move the cam from the second position toward the first position such that the elongate flexible implant decreases in length.

For yet another example, the change in length of the elongate flexible implant can include flexing longitudinally such that elongate flexible implant increases in length or decreases in length depending on the movement of the scapula. For still another example, the change in length of the elongate flexible implant can be configured to limit movement of the scapula. For yet another example, the elongate flexible implant can be configured to automatically flex in response to arm movement of the person that accompanies the movement of the scapula. For another example, the surgical system can include a position limiter configured to limit the elongate flexible implant from flexing beyond a maximum amount. For still another example, the elongate flexible implant can include a hydrogel and a braided polyethylene. For yet another example, the elongate flexible implant can have a stiffness in a range of about 10 N/mm to about 300 N/mm. For another example, the elongate flexible implant can have a stiffness in a range of about 20 N/mm to about 100 N/mm. For yet another example, the elongate flexible implant can have a diameter in a range of about 5 mm to about 10 mm.

For another example, the surgical system can include a second elongate flexible implant configured to be implanted in the body of the person, the second elongate flexible implant can include a third terminal end and a fourth terminal end, the surgical system can also include a second cam configured to be implanted in the body of the person such that the cam and the second cam are each implanted in the body of the person, and, with the first terminal end attached to the rib, the second terminal end attached to the scapula, and the fourth terminal end attached to the scapula, the second elongate flexible implant is configured to extend along an exterior surface of the second cam. In some embodiments, the third terminal end of the second elongate flexible implant can be configured to be attached to a different rib than the elongate flexible implant. In some embodiments, the third terminal end of the second elongate flexible implant can be configured to be attached to a same rib as the elongate flexible implant.

In another embodiment, a surgical system includes a cam configured to be implanted in a body of a person. The cam is configured to attach to a scapula or a rib of the person. The surgical system also includes an elongate flexible implant configured to be implanted in the body of the person with a length of the elongate flexible implant extending along an exterior surface of the cam. The elongate flexible implant is configured to automatically change in length in response to movement of the scapula, and the changing in length of the elongate flexible implant is configured to control the movement of the scapula.

The surgical system can have any number of variations. For example, the elongate flexible implant can be configured to be implanted in the person with a terminal end of the elongate flexible implant attached to a rib of the person. For another example, the cam can be configured to automatically move in a first direction with the movement of the scapula caused by the arm movement of the person, the cam moving in the first direction can correspond to the change in length of the elongate flexible implant being an increase a length of the elongate flexible implant, the cam can be configured to automatically move in a second direction with another movement of the scapula, the second direction can be opposite to the first direction, and the cam moving in the second direction can correspond to the change in length of the elongate flexible implant being a decrease in length of the elongate flexible implant. For yet another example, the surgical system can include a position limiter configured to limit the elongate flexible implant from flexing beyond a maximum amount. For still another example, the elongate flexible implant can include a hydrogel and a braided polyethylene. For another example, the elongate flexible implant can have a stiffness in a range of about 10 N/mm to about 300 N/mm. For yet another example, the elongate flexible implant can have a stiffness in a range of about 20 N/mm to about 100 N/mm. For still another example, the elongate flexible implant can have a diameter in a range of about 5 mm to about 10 mm. For another example, the surgical system can include a second cam configured to be implanted in the body of the person, the second cam can be configured to attach to the other of the scapula and the rib of the person, the surgical system can also include a second elongate flexible implant configured to be implanted in the body of the person with a length of the second elongate flexible implant extending along an exterior surface of the second cam, the second elongate flexible implant can be configured to automatically change in length in response to the movement of the scapula, and the change in length of the second elongate flexible implant can be configured to control the movement of the scapula in cooperation with the change in length of the elongate flexible implant.

In another aspect, a surgical method is provided that in one embodiment includes attaching a first terminal end of a flexible implant to a first body structure of a person, and attaching a second terminal end of the flexible implant to a second body structure of the person. The flexible implant, with the first and second terminal ends attached, is configured to affect motion of a scapula of a person with respect to a thorax of the person.

The surgical method can vary in any number of ways. For example, the flexible implant can be configured to change in length in response to movement of the scapula of the person accompanying arm movement of the person, the change in length of the flexible implant changing a force applied by the flexible implant to the scapula.

For another example, the first body structure can be a rib of the person, and the second body structure can be the scapula of the person. In some embodiments, attaching the first terminal end can include attaching the first terminal end of the flexible implant directly to the rib of the person. In some embodiments, attaching the first terminal end can include attaching the first terminal end of the flexible implant indirectly to the rib of the person using a grommet attached to the rib of the person. In some embodiments, attaching the second terminal end can include attaching the second terminal end of the flexible implant directly to the scapula of the person. In some embodiments, attaching the second terminal end to the scapula can include attaching the second terminal end to an inferior tip of the scapula. In some embodiments, the surgical method can include attaching a cam to the scapula of the person, the cam can be configured to move with the scapula, the flexible implant can extend along an exterior surface of the cam, and attaching the second terminal end can include attaching the second terminal end of the flexible implant indirectly to the scapula of the person via the second terminal end being attached to the cam. The cam can move in a first direction, and the flexible implant can increase in length, with the movement of the scapula, and after the movement of the cam in the first direction, the cam can be configured to move in a second, opposite direction with movement of the scapula accompanying another arm movement of the person, and the flexible implant decreasing in length simultaneously with the movement of the cam in the second direction.

For another example, the flexible implant can include a hydrogel and a braided polyethylene. For yet another example, the flexible implant can have a stiffness in a range of about 10 N/mm to about 300 N/mm. For still another example, the flexible implant can have a stiffness in a range of about 20 N/mm to about 100 N/mm. In some embodiments, the flexible implant can have a diameter in a range of about 5 mm to about 10 mm.

For still another example, the surgical method can also include attaching a cam to the rib of the person, and the flexible implant can extend along an exterior surface of the cam during the movement of the scapula. For another example, the first body structure can be a first muscle of the person, and the second body structure can be a second muscle of the person. In some embodiments, attaching the first terminal end to the second muscle can include attaching the first terminal end superior to an inferior tip of the scapula. In some embodiments, the flexible implant can include a mesh.

For yet another example, the movement of the scapula can include scapulothoracic motion. For another example, the first body structure can be a muscle of the person, and the second body structure can be a rib or a scapula of the person.

For still another example, the surgical method can include attaching a third terminal end of a second flexible implant to a the person, and attaching a fourth terminal end of the second flexible implant to the scapula of the person. In some embodiments, the surgical method can also include attaching a cam to the scapula of the person, and the cam can be configured to move with the scapula, and the flexible implant can extend along an exterior surface of the cam during the movement of the scapula. In some embodiments, attaching the third terminal end can include attaching the third terminal end of the second flexible implant directly to the rib of the person. In some embodiments, attaching the third terminal end can include attaching the third terminal end of the second flexible implant indirectly to the rib of the person using a grommet attached to the rib of the person.

BRIEF DESCRIPTION OF DRAWINGS

This disclosure will be more fully understood from the following detailed description taken in conjunction with the accompanying drawings, in which.

DETAILED DESCRIPTION

Figure 1:
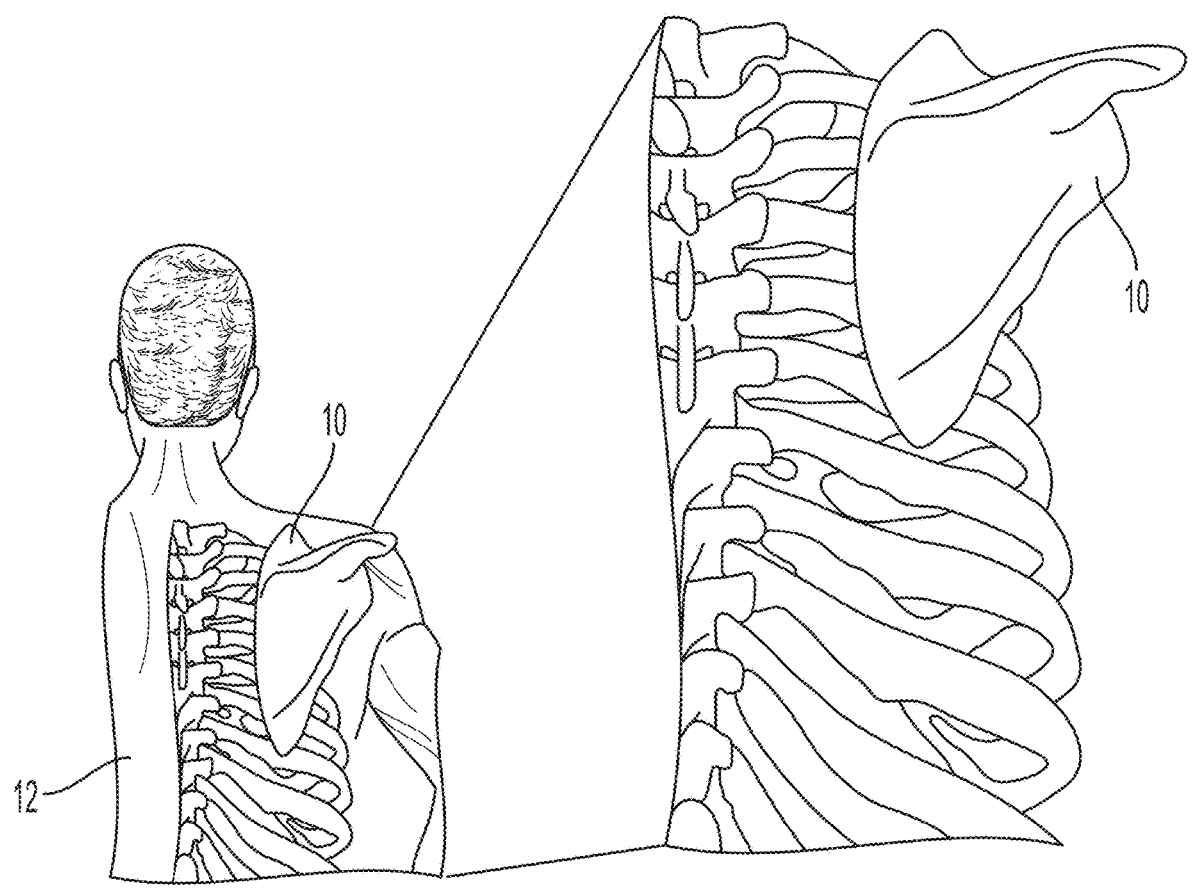
FIG. 1 is a rear view of a patient including ribs and a scapula.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, scapular tethers and methods of using scapular tethers are provided. A tether is configured to be implanted in a body of a patient and to control movement of the patient's scapula. The tether may thus help treat scapular dyskinesis, reduce patient pain, allow for normal or near-normal arm function, and/or help prevent a rotator cuff tear or other shoulder injury from occurring or getting worse by helping the scapula move normally and/or be positioned normally. Scapular dyskinesis may be a cause of a patient's shoulder complication(s), such as pain, restricted arm movement, joint instability, and rotator cuff tears, rather than a symptom of the shoulder complication(s). The tether may thus help treat the cause of a patient's shoulder complication(s) by treating scapular dyskinesis instead of the traditional approach of treating the patient's shoulder complication(s) which, as discussed above, are not always effective. The tether does not require the patient to wear a shirt or other wearable that pushes on the scapula to treat scapular dyskinesis according to various traditional treatment approaches, which can be uncomfortable, obtrusive, and inconvenient for the patient to wear as well as of limited effectiveness. The tether is internal treatment, unlike an external wearable, so the patient does not need to remember to wear a wearable on a regular basis and experience the wearable's various drawbacks.

In an exemplary embodiment, the tether is configured to be attached to at least one body structure in a patient. The implantation of the tether does not require moving tendons or muscles in the patient's back, unlike some traditional approaches that address scapular dyskinesis. In some embodiments the tether can be attached to two different body structures. For example, the tether can be configured to be attached to a rib of the patient and to a scapula of the patient with one end of the tether attached to the rib and an opposite end of the tether attached to the scapula. For another example, the tether can be configured to be attached to a first muscle of the patient and to a second muscle of the patient with one end of the tether attached to the first muscle and an opposite end of the tether attached to the second muscle. For yet another example, the tether can be configured to be attached to a muscle of the patient and to one of a rib of the patient and a scapula of the patient with one end of the tether attached to the muscle and an opposite end of the tether attached to the one of the rib and the scapula. In some embodiments the tether can be attached to a single body structure. For example, the tether can be configured to be attached to a muscle of the patient with one end of the tether attached to the muscle at a first location along the muscle and an opposite end of the tether attached to the muscle at a second location along the muscle.

The tether attached to the at least one body structure is configured to control the movement of the scapula. The tether includes a flexible member configured to, when implanted in the patient, flex in response to movement of the patient's scapula accompanied by arm movement of the patient. The tether is configured to address scapular dyskinesia by controlling the motion of the scapula. In an exemplary embodiment, the tether is configured to control scapular motion by preventing an inferomedial corner of the scapula from rotating up and outward (superiorly and dorsally).

Figure 2:
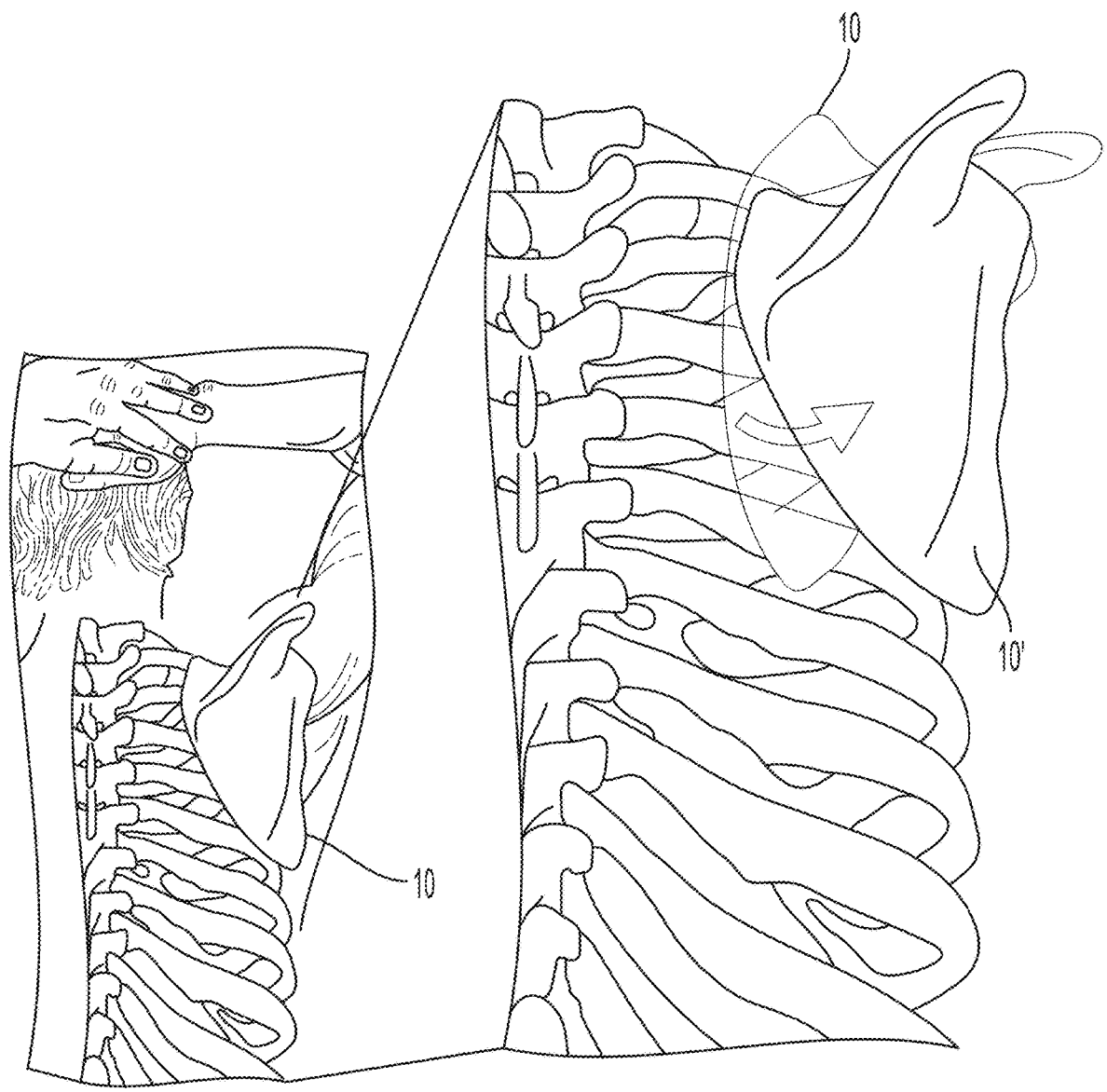
FIG. 2 is a rear view of the patient of FIG. 1 showing one embodiment of normal movement of the scapula.

FIG. 1 illustrates a scapula 10 of a person 12 (a person is also referred to herein as a patient) at a normal resting position. FIG. 2 illustrates movement of the scapula from the normal resting position (scapula labeled with reference numeral 10) to a normal subsequent position (scapula labeled with reference numeral 10') accompanying arm motion. Normal scapular movements include upward/downward rotation around an axis perpendicular to the scapular body, internal/external rotation around a vertical axis created by the medial scapular border, anterior/posterior tilt of around a horizontal axis created by the scapular spine, upward/downward sliding of the scapula on a thorax, and medial/lateral sliding of the scapula around a curvature of the thorax. From a clinical standpoint, these movements are generally coupled together to describe common patterns such as scapular retraction (external rotation, posterior tilt, upward rotation and medial translation), protraction (internal rotation, anterior tilt, downward rotation and lateral translation), and shrug (upward translation, anterior tilt, and internal rotation).

Figure 3:
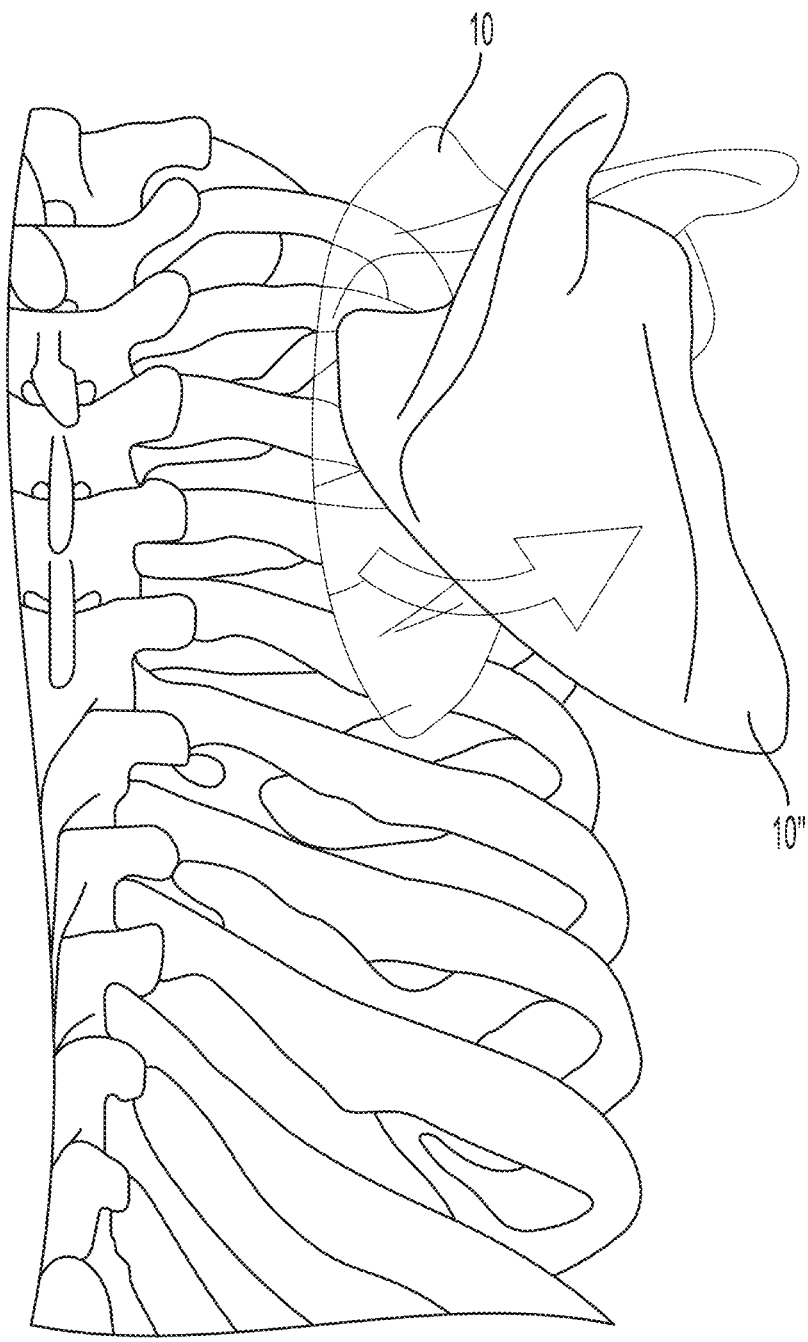
FIG. 3 is a rear view of the patient of FIG. 1 showing one embodiment of abnormal movement of the scapula.

FIG. 3 illustrates movement of the scapula from the normal resting position (scapula labeled with reference numeral 10) to an abnormal subsequent position (scapula labeled with reference numeral 10") accompanying the same arm motion as FIG. 2. In the abnormal subsequent position of FIG. 3, the inferomedial corner of the scapula has undesirably rotated up and outward (superiorly and dorsally). The scapular dyskinesis of FIG. 3 can be due to laxity, muscular or tendinous insufficiency, or other cause(s).

Figure 4:
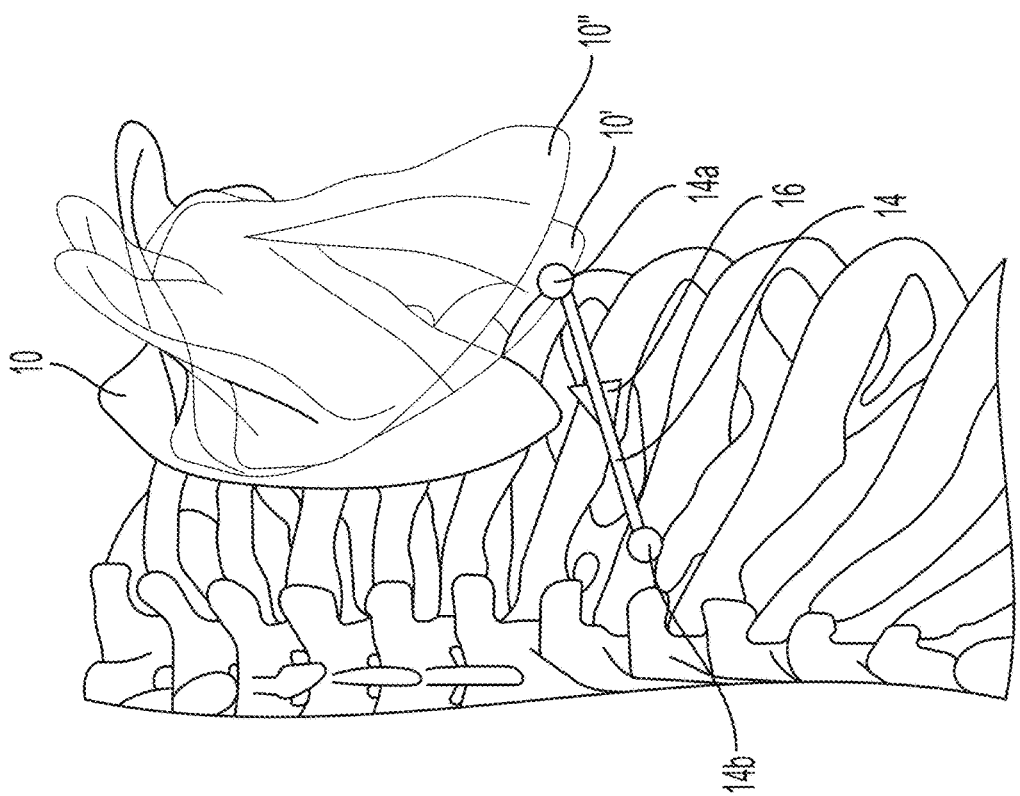
FIG. 4 is a rear view of a patient including ribs and a scapula with one embodiment of a tether attached to the scapula and one of the ribs.

FIG. 4 illustrates one embodiment of a tether 14 and movement of the scapula of FIG. 3 from the normal resting position (scapula labeled with reference numeral 10) to the normal subsequent position (scapula labeled with reference numeral 10') accompanying the same arm motion as FIGS. 2 and 3. Instead of the scapula moving to the abnormal subsequent position (scapula labeled with reference numeral 10") as in FIG. 3, the tether 14 exerts a force on the scapula, shown by an arrow 16, to control the movement of the scapula such that the scapula is urged to not move beyond the normal subsequent position (scapula labeled with reference numeral 10') of FIG. 2 that a patient experiences without scapular dyskinesis. The tether 14 has thus helped hold the scapula in place so as to prevent the inferomedial corner of the scapula from undesirably rotating up and outward (superiorly and dorsally).

The normal and abnormal subsequent positions of the scapula of FIGS. 2-4 are examples. Different people will have normal and abnormal subsequent positions of the scapula similar to those of FIGS. 2-4, but the normal and abnormal subsequent positions of the scapula for a particular person vary based on, e.g., the person's particular anatomy and the person's scapular dyskinesis. Additionally, different abnormal subsequent positions of the scapula are possible for a person with scapular dyskinesis for different motions of the person's arm.

FIG. 4 illustrates a single tether 14 attached to the person's scapula. However, a person can have a plurality of tethers attached to a single scapula of the person. In some instances a single tether may be insufficient to guide movement of the scapula away from an abnormal subsequent position of the scapula and toward a normal subsequent position of the scapula, such as if the scapula's abnormal movement is especially severe and cannot be sufficiently counteracted by a force provided by the single tether and/or is in multiple planes of motion that cannot all be sufficiently counteracted by a force provided by the single tether. Attaching a plurality of tethers to the scapula may allow for treatment if the scapula's abnormal movement is especially severe, or multidirectional, by allowing the multiple tethers to each provide a force that together can sufficiently counteract the scapula's abnormal movement and/or if the scapula's abnormal movement is in multiple planes of motion by allowing each of the tethers to provide a force that counteracts motion in one of the planes of motion.

Figure 5:
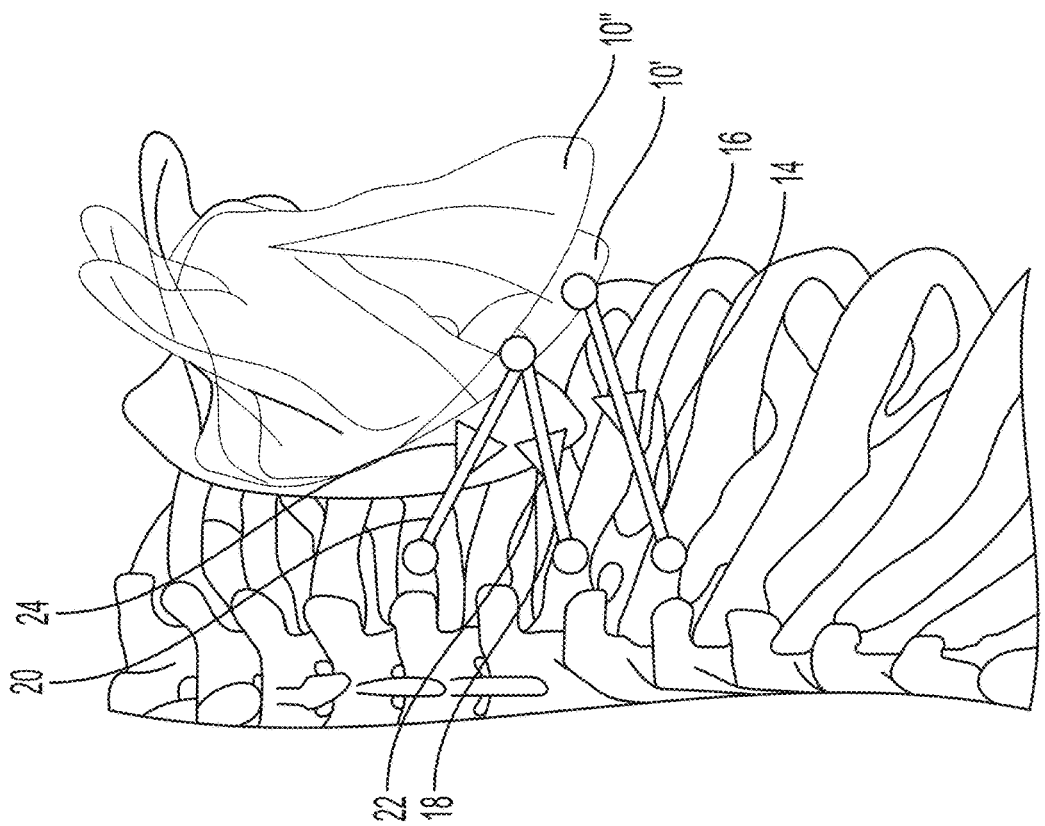
FIG. 5 is a rear view of a patient including ribs and a scapula, embodiments of a plurality of tethers being attached to the scapula and the ribs.

FIG. 5 illustrates one embodiment in which a plurality of tethers 14, 18, 20 are attached to the scapula. The tether 14 is the same as the tether 14 in FIG. 4. Two additional tethers 18, 20 are attached to the scapula in the embodiment of FIG. 5. Forces on the scapula provided by the tethers 18, 20 are shown by arrows 22, 24, respectively, and cooperate with the force on the scapula provided by the tether 14, shown by arrow 16, to control the movement of the scapula such that the scapula is urged to move to the normal subsequent position (scapula labeled with reference numeral 10') of FIG. 2 that a person experiences without scapular dyskinesis.

The tether 14 of FIGS. 4 and 5 is attached to the scapula of a person and to a rib of the person. A first terminal end 14a of the tether 14 is attached to the scapula, and a second terminal end 14b of tether 14 is attached to the rib. The first and second terminal ends 14a, 14b of the tether 14 can be directly or indirectly attached to the scapula and the rib, respectively, as discussed further below. Each of the additional tethers 18, 20 of FIG. 5 are similarly attached to the scapula of a person and to a rib of the person with one terminal end attached to the scapula and another terminal end attached to a rib. Each of the tethers 14, 18, 20 is attached to a different rib in the illustrated embodiment of FIG. 5, but one or more of the tethers 14, 18, 20 can be attached to a same rib as at least one of the other tethers 14, 18, 20.

A tether, such as the tethers 14, 18, 20, can be attached to a scapula at any of a variety of locations. In an exemplary embodiment, the tether is attached to an inferior tip of the scapula, also referred to as an inferior angle of a scapula. The scapular bone is relatively thin at the inferior tip of the scapula, which may facilitate creation of a portal through the bone for attachment of the tether to the bone, such as by tying, knotting, etc., with or without use of a cam and/or a grommet (each discussed further below). A size of the portal varies based on a size, e.g., a diameter, of the tether. The scapular bone at the edge of the scapula is thicker and stronger than at the inferior tip of the scapula, so the portal will not tend to crack or break through the edge of the scapula. The tether can be attached at the inferior tip of the scapula at a variety of distances from the edge of the scapula. A portal need not be formed through the scapula to attach the tether to the scapula. For example, the tether can be adhered with an adhesive to a surface of the scapula.

Figure 6:
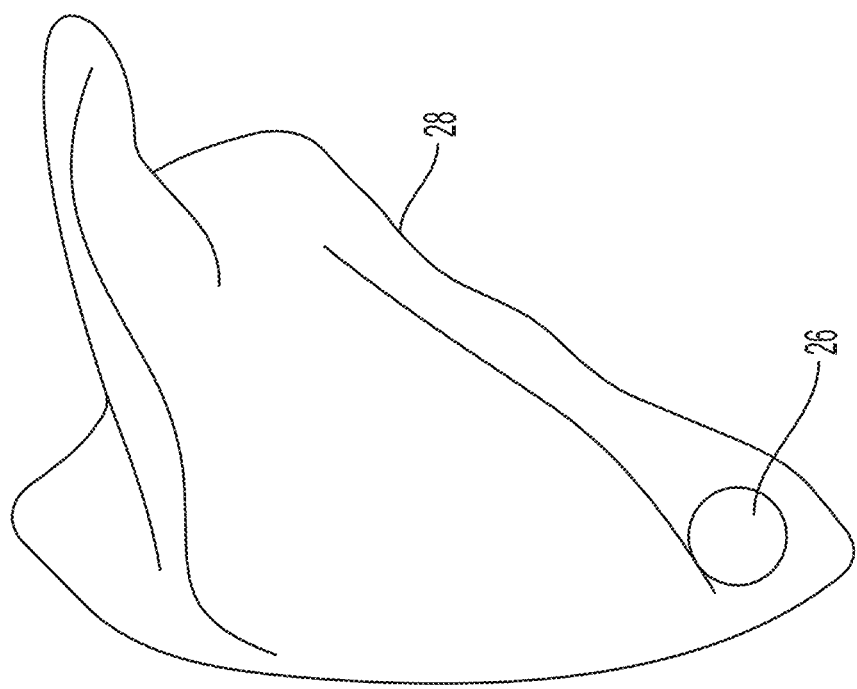
FIG. 6 is a rear view of a right scapula showing one embodiment of attachment area thereon.

FIG. 6 illustrates one embodiment of a tether attachment area 26 at an inferior tip of a scapula 28. The attachment area 26 in this illustrated embodiment is at least about 1 cm from the edge of the scapula 28, but other distances from the edge of the scapula 28 are possible based on surgeon discretion and/or other factor(s). A person skilled in the art will appreciate that a value may not be precisely at a value but nevertheless be considered to be about that value for any of a variety of reasons, such as sensitivity of measurement equipment and manufacturing tolerances.

A tether, such as the tethers 14, 18, 20, can be attached to a rib at any of a variety of locations. In general, where the tether is attached to a rib depends on the scapular motion desired to be controlled by the tether. Similarly, the rib to which the tether is attached depends on the scapular motion desired to be controlled by the tether. Which rib the tether is attached to and where the tether is attached to at that rib, in combination with where the tether is attached to the scapula, defines a direction of the force that the tether will exert on the scapula to control the scapula's movement. A maximum length of the tether can affect to which rib the tether is attached because attaching the tether to a rib too far away from the scapula may not allow the tether to change in length sufficiently to allow for desired scapular motion. A person's anatomy can affect to which rib the tether is attached because certain anatomies may have different ribs closer to the scapula and/or more convenient for a surgeon to access during performance of a surgical procedure in which the tether is attached to the rib. A tether can be attached to a rib in a variety of ways, such as by being tied thereto, adhered thereto using adhesive, using a grommet, or other ways.

The scapula normally covers ribs two through seven. Thus, in an exemplary embodiment in which the tether is attached to a rib, the tether is attached to one of ribs one through eight. Attaching the tether to rib eight may be beneficial because rib eight is typically more easily surgically accessible than other ribs, rib eight has close proximity to an inferior tip of a person's scapula when the person's arm is at a side of the person such that one small incision can be made to work on both the scapula and the rib, and the tether would be attached to rib eight and to the scapula approximately in a longitudinal plane of the person's body. A person skilled in the art will appreciate that a tether may not be precisely in a longitudinal plane of a person's body but nevertheless be considered to be in the longitudinal plane of the person's body for any of a variety of reasons, such as sensitivity of measurement equipment and manufacturing tolerances. Attaching the tether to rib seven may be beneficial because a single hole can be formed, e.g., drilled or otherwise formed, through a person's scapula to provide access to rib seven below. The tether attached to rib seven can be placed in an approximately dorsal/ventral direction so as to be approximately perpendicular to a longitudinal plane of the person's body. Dorsal motion of scapula may thus be easily controlled with the tether attached to rib seven.

In some embodiments, a tether attached to a person's rib can be placed through a transverse process of the person's spine (T6, T7, or T8). Such placement may reduce likelihood of boney fracture.

FIGS. 1-5 illustrate movement of the right scapula and, for FIGS. 4 and 5, the tether(s) attached to the right scapula, e.g., because the right scapula is experiencing scapular dyskinesis. The left scapula can similarly move and can similarly have a tether attached thereto, e.g., in cases where the left scapula is experiencing scapular dyskinesis. A person can have at least one tether attached to their right scapula and no tethers attached to their left scapula, can have at least one tether attached to their left scapula and no tethers attached to their right scapula, or can have at least one tether attached to their right scapula and at least one tether attached to their left scapula.

The tethers 14, 18, 20 of FIGS. 4 and 5 each include a flexible member and, in these illustrated embodiments, each include an elongate flexible member. The elongate flexible member is configured to flex to move between a normal or initial position, corresponding to the normal resting position of the scapula, and an extended or flexed position, corresponding to the normal subsequent position of the scapula. The flexed position varies based on different arm motions of the person. The elongate flexible member thus has a plurality of possible flexed positions, each corresponding to a different scapula position and a different type and amount of arm movement. In the relaxed position the elongate flexible member has a first length. In the extended position the elongate flexible member has a second length that is different than the first length. The flexing of the elongate flexible member in moving from the relaxed position to the flexed position causes the length to change. The relaxing of the elongate flexible member in moving from the flexed position toward the relaxed position causes the length to change again.

The elongate flexible member can be made from a variety of biocompatible materials. For example, the elongate flexible member can include a braided polyethylene, e.g., ultra-high-molecular-weight polyethylene (UHMWPE) or other polyethylene, and a hydrogel core. The hydrogel core can increase the flexibility of the elongate flexible member as compared to the braided polyethylene without a hydrogel core. The hydrogel core can be silicone or other hydrogel. A proportion of the hydrogel core to an outer diameter of the elongate flexible member, as compared to a proportion of the braided polyethylene to the outer diameter of the elongate flexible member affects the flexibility of the elongate flexible member. In general, the greater the proportion of the hydrogel core to the outer diameter of the elongate flexible member, the greater the flexibility of the elongate flexible member. Elongate flexible members with different stiffnesses are thus possible. For another example, the elongate flexible member can be formed of an elastomeric and biocompatible material such as a biocompatible polymer, e.g., UHMWPE, polytetrafluoroethylene (PTFE), nylon, polyurethane, a thermoplastic elastomer such as HYTRL™, etc. Different stiffnesses of the elongate flexible member are possible with different diameters of the elastomeric and biocompatible material and based on the elastomeric properties of a particular elastomeric and biocompatible material. For yet another example, the elongate flexible member can be formed of a biologic graft or construct, such as a gracilis hamstring tendon or a cadaver-sourced allograft tendon.

Regardless of the material of a tether, a position limiter can be configured to limit the tether from increasing in length beyond a maximum amount. The position limiter can thus help control movement of the scapula to which the tether is attached (or whose movement causes flexing of the tether, in embodiments in which the tether is only attached to soft tissue and not bone) by preventing the tether from flexing beyond a certain point, thereby preventing the scapula from moving beyond a certain corresponding point. A flexible member can become stiff over time as the flexible member repeatedly moves in response to repeated arm movements. The position limiter may help reduce any adverse effect of the tether's decreased stiffness by providing a predictable maximum amount of stiffness for the tether over the course of the elongate flexible member's implanted use.

The position limiter can have a variety of configurations. For example, the position limiter can include a substantially rigid elongate member, e.g., a wire, a cable, etc. A person skilled in the art will appreciate that a member may not be fully rigid but nevertheless be considered to be substantially rigid due to any number of factors, such as manufacturing tolerances and sensitivity of measurement equipment. The substantially rigid elongate member can be formed of any of a variety of materials, such as stainless steel, a shape memory material (e.g., Nitinol, etc.), etc. The substantially rigid elongate member is configured to move between a slackened configuration and a taut configuration. With the tether in the relaxed position, the substantially rigid elongate member is in the slackened configuration. In the slackened configuration, the substantially rigid elongate member is not fully extended longitudinally but instead has some slack available to allow for the tether to flex, e.g., to extend in length and move from the relaxed position to the flexed position. As the tether flexes, the substantially rigid elongate member moves from the slackened configuration toward the taut configuration. When the substantially rigid elongate member reaches the taut configuration, all the slack has been eliminated and the substantially rigid elongate member is fully extended longitudinally. The substantially rigid elongate member moving to the taut configuration stops the flexing of the tether. The tether is thus configured to flex freely until the substantially rigid elongate member reaches the taut configuration. The substantially rigid elongate member therefore limits the tether from increasing in length beyond a maximum amount defined by a length of the substantially rigid elongate member.

The substantially rigid elongate member can extend along an exterior of the tether. The same attachment points at the rib/scapula, first muscle/second muscle, or first muscle/first muscle for the tether can be used for the right elongate member. In other embodiments, the substantially rigid elongate member can extend through the tether. The substantially rigid elongate member can thus be a core of the tether. In embodiments in which the tether includes a hydrogel core, the substantially rigid elongate member can extend through the hydrogel core.

For another example, the position limiter can include a bumper configured to abut the tether and/or a scapula once the tether has flexed a certain amount to increase its length to a certain length. The bumper can be attached to the scapula or to another bone such as a rib. The bumper is configured to limit the tether from increasing in length beyond a maximum amount by bumping against the tether and/or the scapula, thereby preventing further movement of the scapula and preventing further flexing of the tether. The bumper can have a variety of configurations. In an exemplary embodiment, the bumper is soft to help prevent the bumper from damaging the tether and/or scapula that the bumper is configured to abut. For example, the bumper can be an inflated balloon or other inflated member. For another example, the bumper can be a rubber or other elastomeric stopper.

Figure 7:
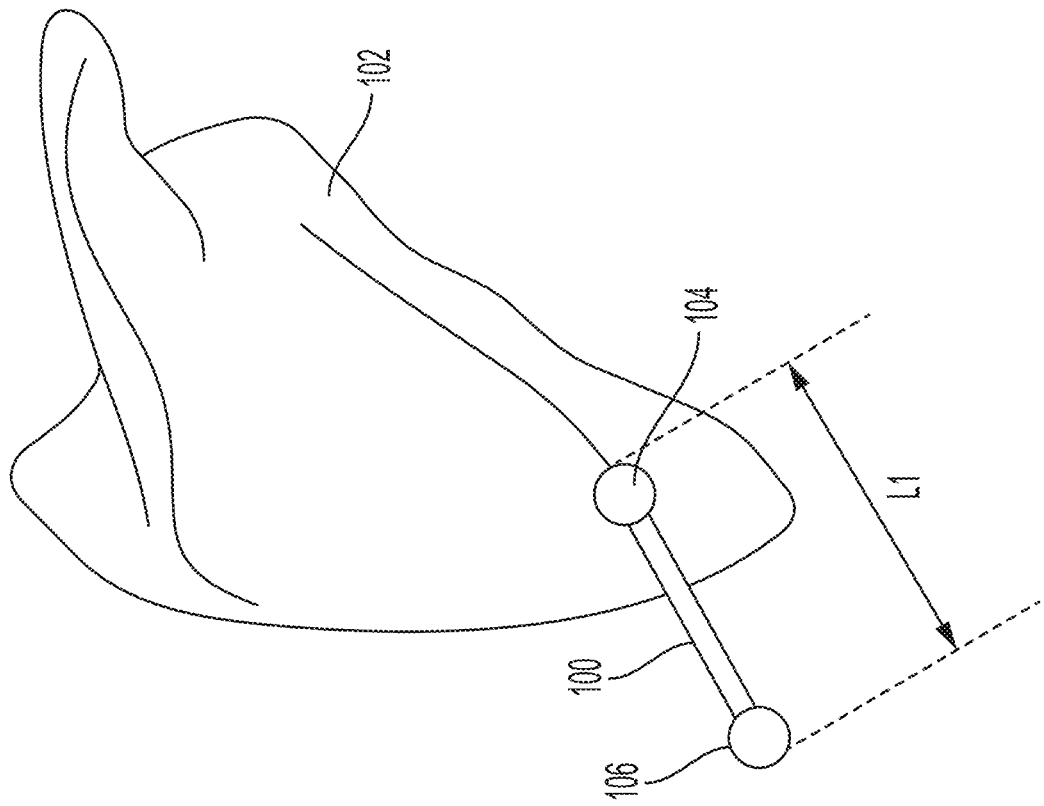
FIG. 7 is a rear view of a right scapula showing another embodiment of tether attached thereto.

FIG. 7 illustrates another embodiment of a tether 100 that includes an elongate flexible member. The elongate flexible member can have a variety of configurations, as discussed herein. The tether 100 in this illustrated embodiment is attached to a scapula 102 and to a rib (not shown) of a person. The tether 100 is attached to the scapula 102 at a first attachment point and to the rib at a second attachment point. A first terminal end 104 of the tether 100 is attached to the scapula 102 at the first attachment point, and a second terminal end 106 of the tether 100 is attached the rib at the second attachment point. The tether 100 can be attached to the scapula 102 and the rib in any of a variety of ways, as discussed herein. The scapula 102 is illustrated in FIG. 7 at a normal resting position. The tether 100 is thus in a normal or initial position in FIG. 7. The tether 100 in the initial position has a first length L1 and exerts a first force on the scapula 102. In an exemplary embodiment, the first force is about zero such that the tether 100 in the initial position exerts substantially no force on the scapula 102, but other first forces are possible based on one or more factors such as a particular desired scapular position and/or motion.

Figure 8:
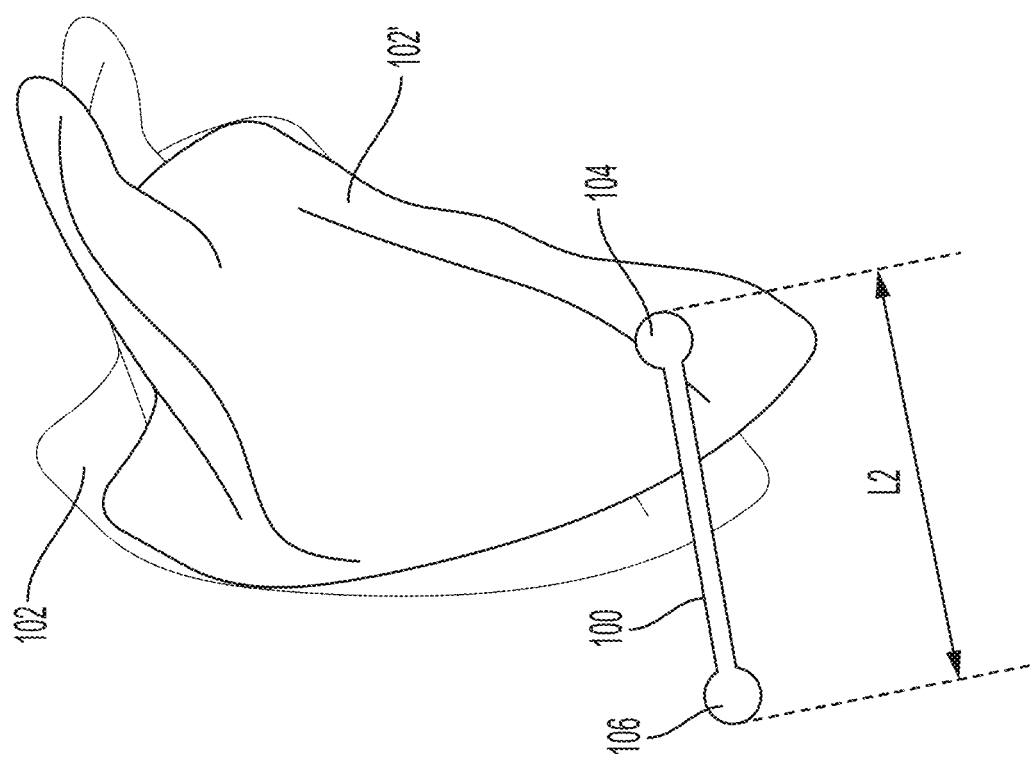
FIG. 8 is a rear view of the scapula and the tether of FIG. 7 with the scapula moved from its position in FIG. 7.

FIG. 8 illustrates movement of the scapula from the normal resting position (scapula labeled with reference numeral 102) to an initial normal position or first normal subsequent position (scapula labeled with reference numeral 102') accompanying arm movement of the person. The rib, and thus the second terminal end 106 of the tether 100, have not moved from FIG. 7 to FIG. 8. The scapula 102, and thus the first terminal end 104 of the tether 100, have moved from FIG. 7 to FIG. 8 relative to the rib and the second terminal end 106 of the tether 100. The movement of the scapula 102 has caused the tether 100 to move from the initial position to a first changed or elongated position and to increase in length from the first length L1 to a second length L2.

Figure 9:
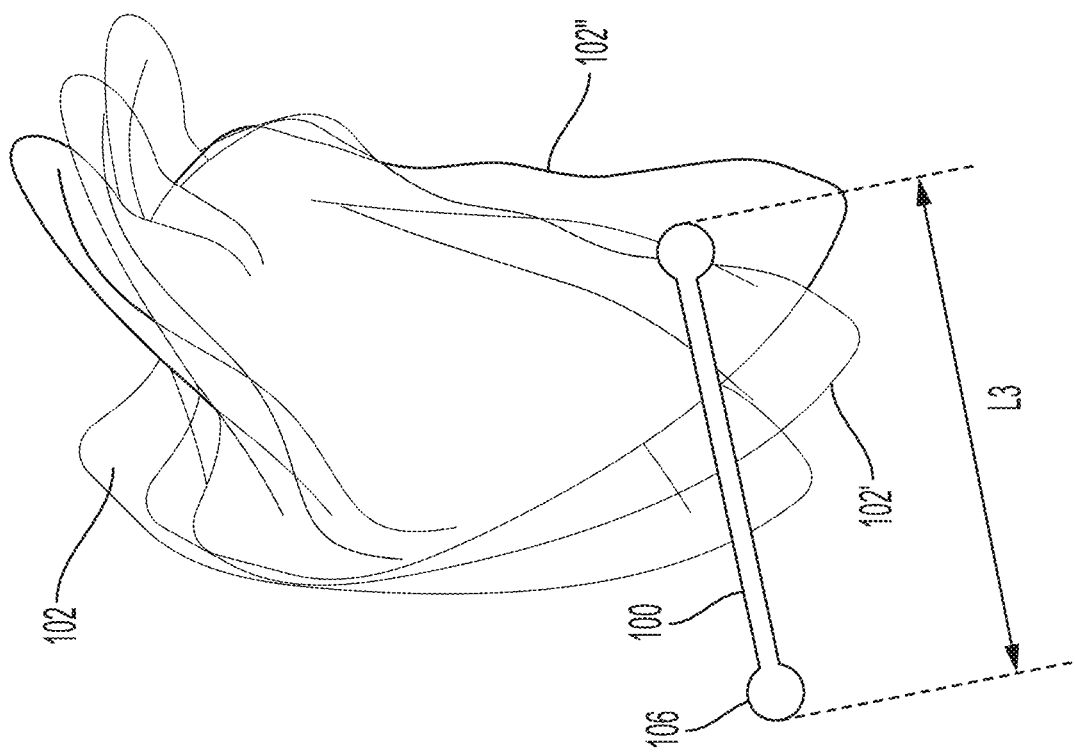
FIG. 9 is a rear view of the scapula and the tether of FIG. 8 with the scapula moved from its position in FIG. 8.

FIG. 9 illustrates movement of the scapula from the first normal subsequent position (scapula labeled with reference numeral 102') to a second normal subsequent position (scapula labeled with reference numeral 102") accompanying arm movement of the person. The rib, and thus the second terminal end 106 of the tether 100, have not moved from FIG. 8 to FIG. 9. The scapula 102, and thus the first terminal end 104 of the tether 100, have moved from FIG. 8 to FIG. 9 relative to the rib and the second terminal end 106 of the tether 100. The movement of the scapula 102 has caused the tether 100 to flex and thus move from the first changed position to a second changed or elongated position and to increase in length from the second length L2 to a third length L3.

Figure 10:
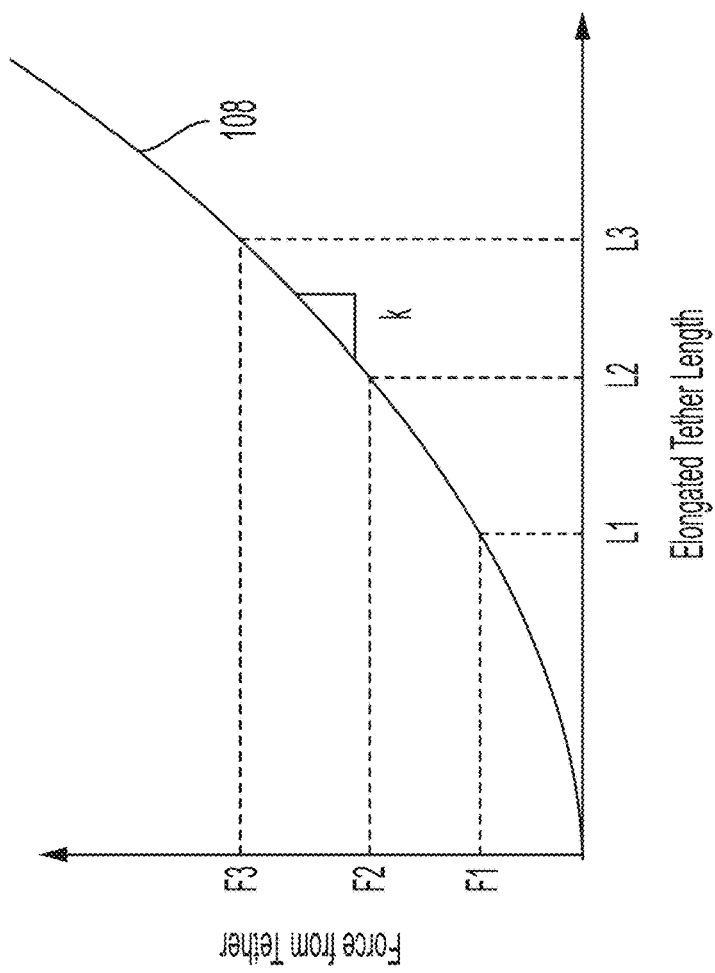
FIG. 10 is a graph showing force versus tether length for the tether of FIGS. 7-9.

FIG. 10 illustrates with respect to FIGS. 7-9 a graph of force from the tether 100 versus length of the tether 100. A first force F1 in the graph corresponds to a force applied to the scapula 102 from the tether 100 with the scapula 100 in the normal resting position (FIG. 7). A second force F2 in the graph corresponds to a force applied to the scapula 102 from the tether 100 with the scapula 102' in the first normal subsequent position (FIG. 8). A third force F3 in the graph corresponds to a force applied to the scapula 102 from the tether 100 with the scapula 102" in the second normal subsequent position (FIG. 9). A curve 108 in the graph shows a force-elongation relationship for the tether 100. As shown in the graph, the more elongated the tether 100, the greater the force exerted by the tether 100 on the scapula 102.

The graph of FIG. 10 also shows a nominal stiffness (stiffness coefficient) k of the tether 100. In general, the more flexible the tether 100 is, the less stiff the tether 100 is and thus the lower the tether's nominal stiffness k. The nominal stiffness k of the tether 100 is chosen to give the desired magnitude of force for the expected change in the tether's length. In an exemplary embodiment, the nominal stiffness k is in a range of about 10 N/mm to about 100 N/mm. Tendons that are undamaged and healthy can have stiffnesses in a range of about 20 N/mm to about 30 N/mm. The tether 100 can thus be configured to mimic the stiffness of an undamaged, healthy tendon by having a stiffness k in a range of about 20 N/mm to about 30 N/mm, can be configured to be less stiff than an undamaged, healthy tendon by having a stiffness k that is less than about 20 N/mm, and can be configured to be more stiff than an undamaged, healthy tendon by having a stiffness k that is greater than about 30 N/mm. Based on a desired motion of the scapula 102 that the tether 100 is configured to help cause, a tether 100 with a particular stiffness coefficient k can be chosen.

In an exemplary embodiment in which the tether 100 includes a looped elongate flexible member and has biomechanical properties that generally correspond to a human tendon's biomechanical properties, the tether 100 has a stiffness of about 300 N/mm and a tensile strength of about 2,000 N. In an exemplary embodiment in which the tether 100 includes a non-looped elongate flexible member and has biomechanical properties that generally correspond to a human tendon's biomechanical properties, the tether 100 has a stiffness in a range of about 20 N/mm to about 100 N/mm.

Figure 11:
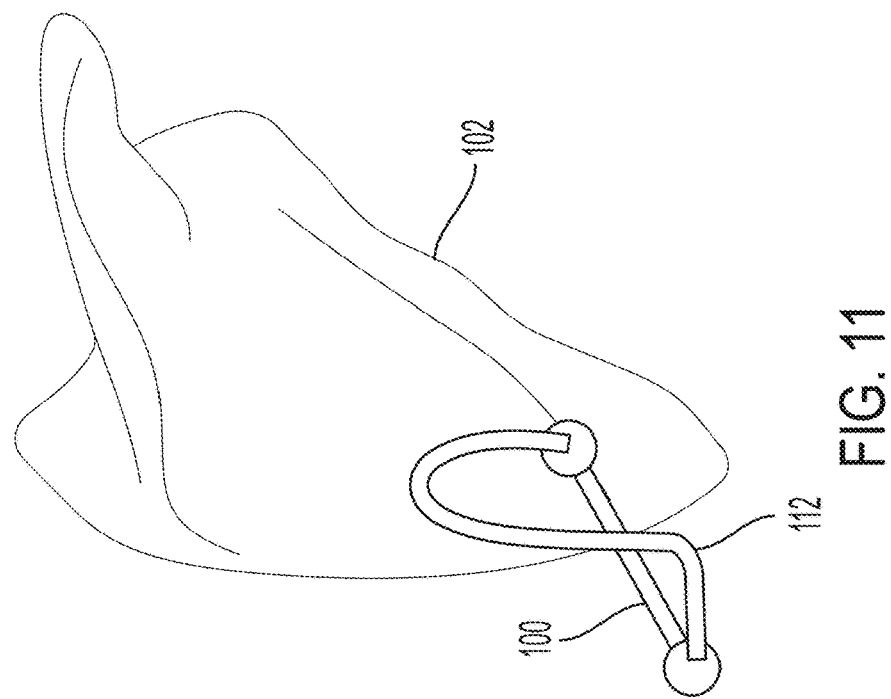
FIG. 11 is a rear view of a right scapula showing the tether of FIG. 7 attached thereto and a position limiter attached thereto.
Figure 13:
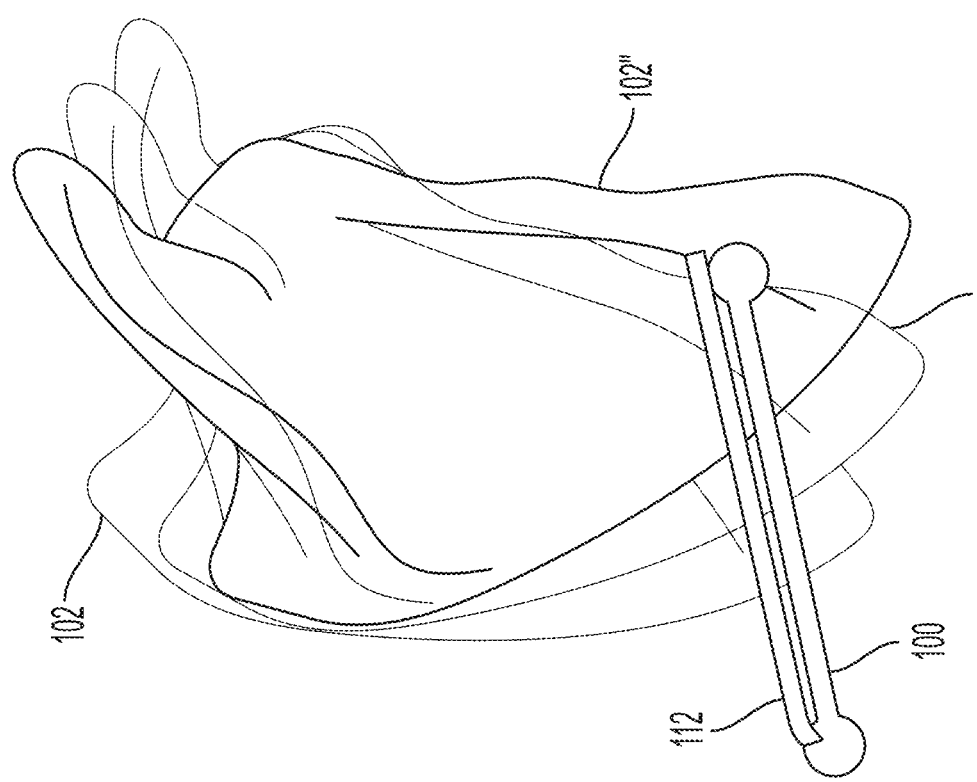
FIG. 13 is a rear view of the scapula, the position limiter, and the tether of FIG. 12 with the scapula moved from its position in FIG. 12.
Figure 12:
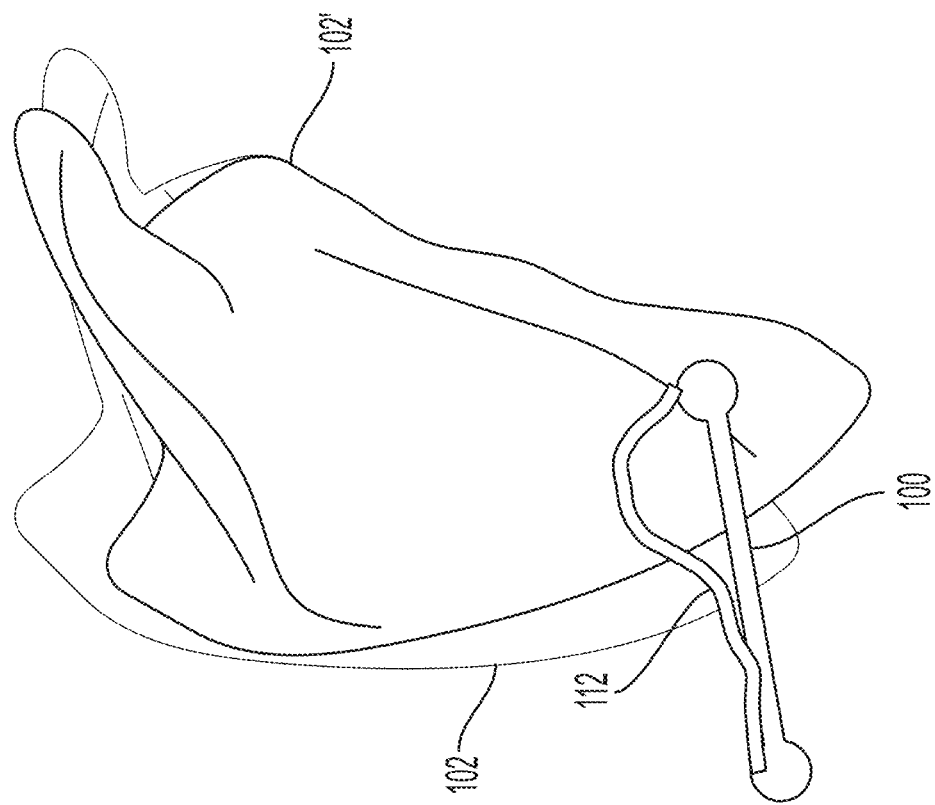
FIG. 12 is a rear view of the scapula, the position limiter, and the tether of FIG. 11 with the scapula moved from its position in FIG. 11.

FIGS. 11-13 illustrate another embodiment in which a position limiter 112 in the form of a substantially rigid elongate member extends along an exterior of the tether 100. The positions of the tether 100 and the scapula 102 in FIGS. 11-13 correspond to the positions of the tether 100 and the scapula 102 in FIGS. 7-9, respectively. With the scapula 102 in the normal resting position and the tether 100 in the initial position (FIG. 11), the position limiter 112 is in a first slackened configuration. The position limiter 112 has an S-shape in the first slackened configuration in this illustrated embodiment but can have other shapes. With the scapula 102' in the first normal subsequent position and the tether 100 in the first elongated position (FIG. 12), the position limiter 112 is in a second slackened configuration. The position limiter 112 has less slack in the second slackened configuration than in the first slackened configuration. The position limiter 112 has a ladle or spoon shape in the second slackened configuration in this illustrated embodiment but can have other shapes in the second slackened configuration. With the scapula 102" in the second normal subsequent position and the tether 100 in the second elongated position (FIG. 13), the position limiter 112 is in a taut configuration. The position limiter 112 is thus preventing the tether 100 from elongating beyond the second elongated position even if the tether 100 would otherwise be capable of flexing to have a length greater than the third length L3 the tether 100 has in the second elongated position of FIG. 13.

Figure 14:
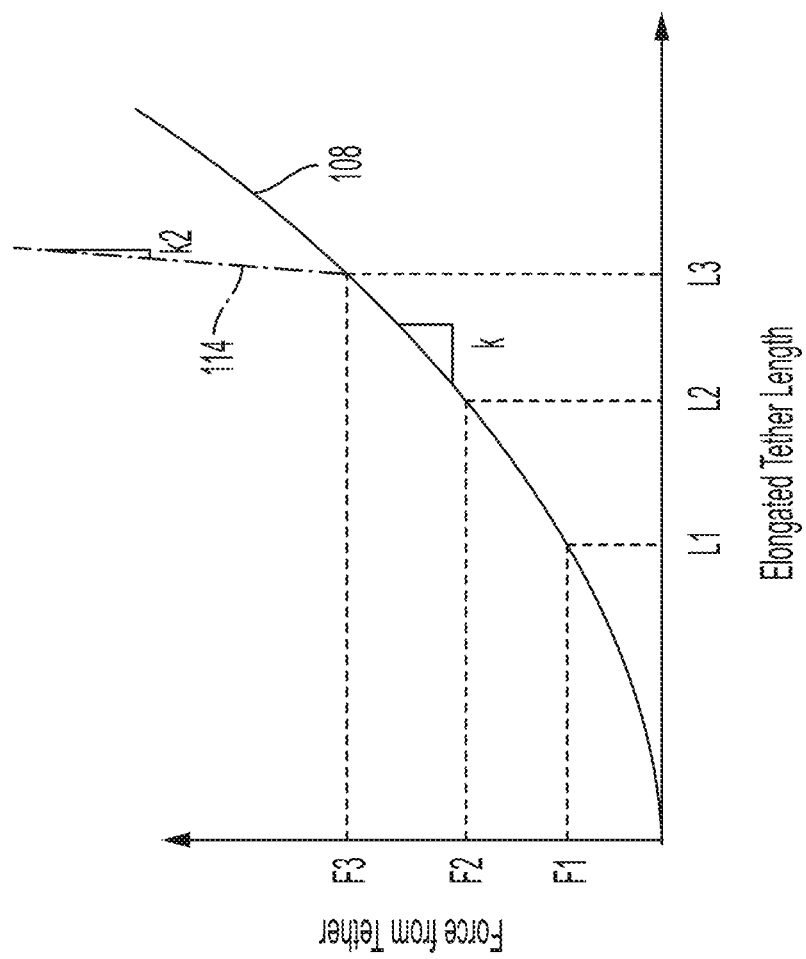
FIG. 14 is a graph showing force versus tether length for the tether of FIGS. 11-13.

FIG. 14 illustrates with respect to FIGS. 11-13 a graph of force from the tether 100 versus length of the tether 100. The graph of FIG. 14 is the same as the graph of FIG. 10 until the tether 100 reaches the third length L3. The force-displacement relationship for the construct including the tether 100 and the position limiter 112 does not follow the curve 108 once the tether 100 reaches the third length L3. The position limiter 112 prevents the construct (tether 100 and position limiter 112) from following the curve 108 once the tether 100 reaches the third length L3. The position limiter 112 has a much greater stiffness k2 than the stiffness k of the tether 100, so high forces are generated, as shown by a second curve 114, that prevent the tether 100 from elongating beyond the third length L3. The high forces prevent the scapula from moving beyond the second normal subsequent position of FIG. 13. The position limiter 112 thus functions as a hard stop to the motion of the scapula.

As mentioned above, a tether can be attached to a bone, e.g., a scapula or a rib, in a variety of ways. In some embodiments, the tether can be directly attached to the bone. For example, the tether can be adhered to a surface of the bone. For another example, a portal can be formed through the bone, and the tether can be secured to the bone at the portal such as by being threaded or otherwise positioned through the portal. For yet another example, the tether can be stapled to the bone. Attaching a tether to bone using a surgical staple may be faster than attaching a tether to bone using a grommet since a portal need not be formed in the bone. In some embodiments, the tether can be indirectly attached to the bone. For example, the tether can be secured to the bone using a suture anchor. Attaching a tether to bone using a suture anchor may be faster than attaching a tether to bone using a grommet since a portal need not be formed in the bone. For another example, the tether can be attached to bone using a cam. For yet another example, a portal can be formed through the bone, and a grommet can be secured at the portal so as to surround the portal. The tether can then be secured to the scapula by being threaded or otherwise positioned through the grommet and thus through the portal. The grommet is configured to help prevent the tether from being damaged by rubbing against the bone, which may be rough, particularly at the edge of the portal. The grommet is also configured to help prevent the bone from being damaged by the tether, such as by the tether "cheese-wiring" or cutting through the bone. The grommet can have a rounded inner surface to help protect the tether from being damaged by the grommet.

The grommet can have a size that allows the tether to extend through a center opening thereof. In an exemplary embodiment, a tether as an elongate flexible member has a diameter in a range of about 5 mm to about 10 mm. The center opening of the grommet can thus have a diameter sized to accommodate a tether having a diameter in a range about 5 mm to about 10 mm. In an exemplary embodiment, an outer diameter of the grommet is in a range of about 15 mm to about 20 mm.

Figure 15:
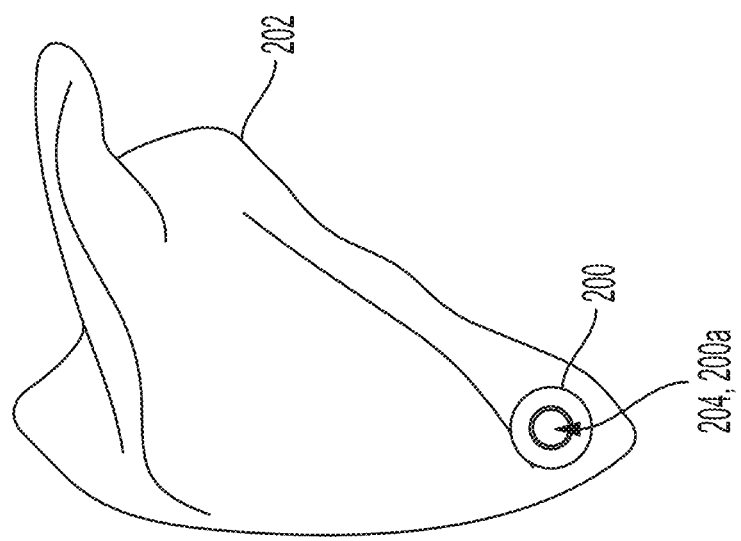
FIG. 15 is a rear view of a scapula with one embodiment of a grommet attached thereto.

FIG. 15 illustrates one embodiment of a grommet 200 secured at a scapula 202 of a person, and in particular at a portal 204 formed through the scapula 202. The grommet 200 is located at an inferior tip of the scapula 202, but as discussed herein, a tether, and thus the grommet, can be attached to a scapula at other scapular locations. A tether is configured to be attached to the scapula 202 by being threaded or otherwise positioned through the portal 204 and a center opening 200a of the grommet 200.

Figure 17:
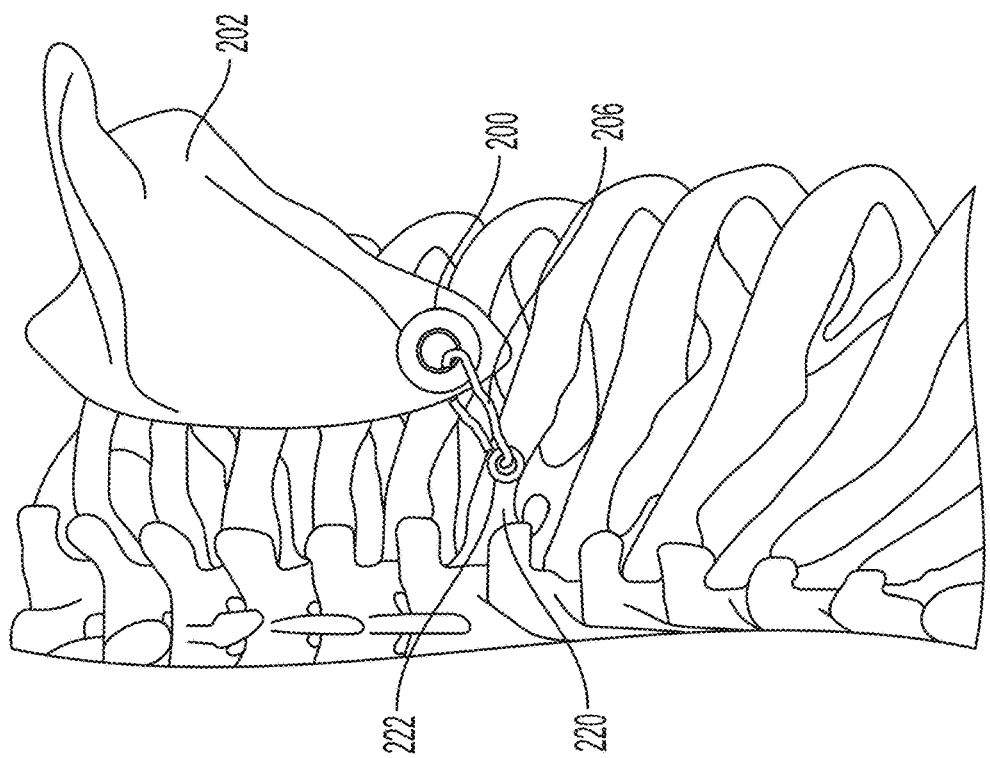
FIG. 17 is a rear view of the scapula, the tether, and the grommet of FIG. 16 with the tether and a second grommet attached to a rib.
Figure 16:
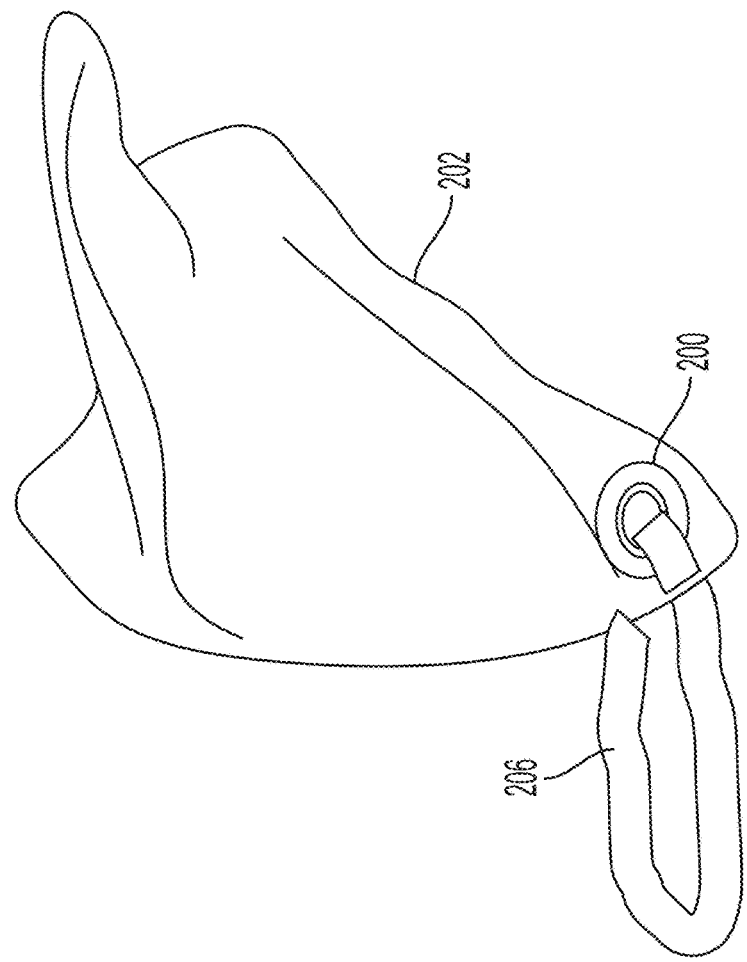
FIG. 16 is a rear view of the scapula of FIG. 15 with another embodiment of a tether extending through the grommet.

FIG. 16 illustrates another embodiment of a tether 206 threaded or otherwise positioned through the portal 204 and the center opening 200a of the grommet 200. FIG. 17 illustrates the tether 206 also attached to a rib 220 of the person using a second grommet 222. The tether 206 in this illustrated embodiment is an elongate flexible member in the form of a loop. The loop allows the tether 206 to be looped through each of the grommets 200, 222.

Figure 19:
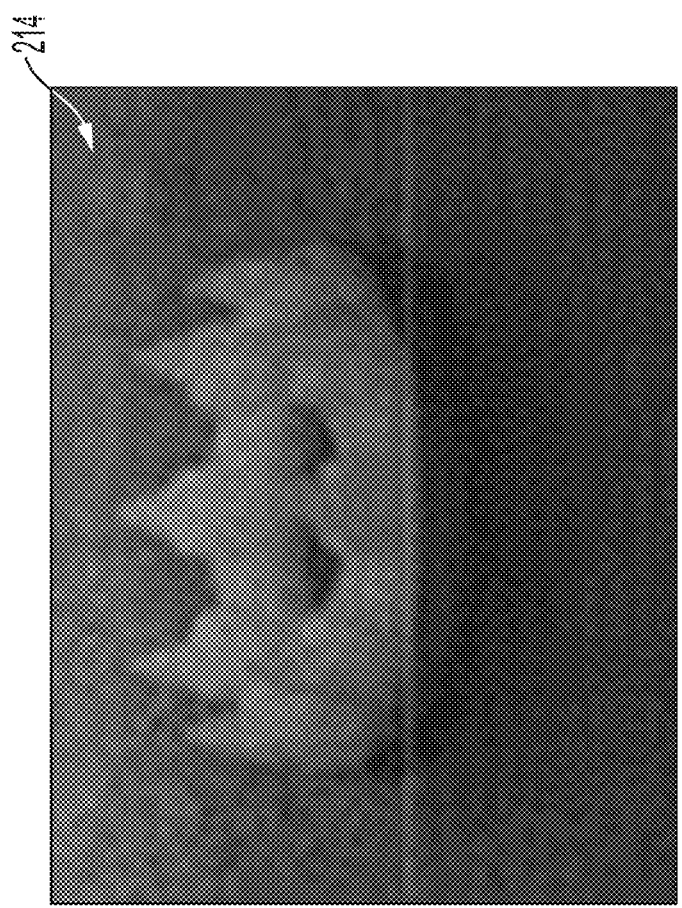
FIG. 19 is a perspective view of yet another embodiment of a grommet.
Figure 18:
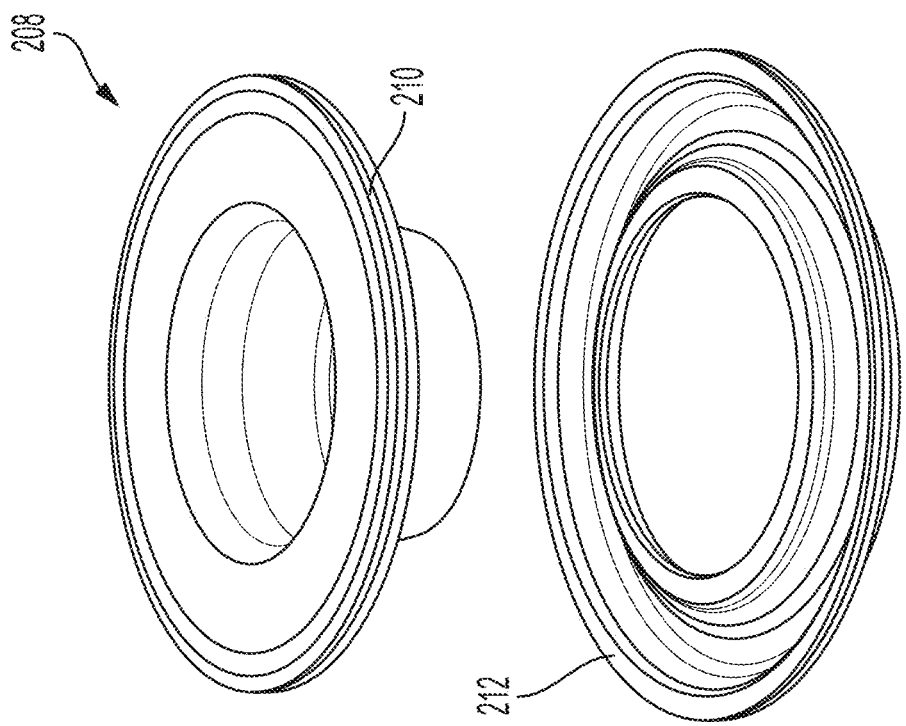
FIG. 18 is a perspective view of another embodiment of a grommet.

The grommets 200, 222 can have a variety of configurations. In some embodiments, a grommet can be a two-piece grommet. FIG. 18 illustrates one embodiment of a two-piece grommet 208. Attached to the scapula, one of the grommet's two pieces 210, 212 can be superficial to the scapula, and the other of the grommet's two pieces 210, 212 can be deep. In some embodiments, a grommet can be a one-piece grommet, for example a spiked washer. FIG. 19 illustrates one embodiment of a one-piece grommet 214 in the form of a spiked washer. In general, larger diameter washers tend to have better holding strengths than smaller diameter washers. The one-piece grommet 214 of FIG. 19 and other embodiments of one-piece grommets are further described in Straight et al., "Soft Tissue Fixation to Bone: A Biomechanical Analysis of Spiked Washers," *The American Journal of Sports Medicine*, Vol. 22, No. 3, 1994, p. 339-343, which is hereby incorporated by reference in its entirety. Attached to the scapula, the spiked side of the one-piece grommet 214 can be on a superficial surface of the scapula.

Figure 21:
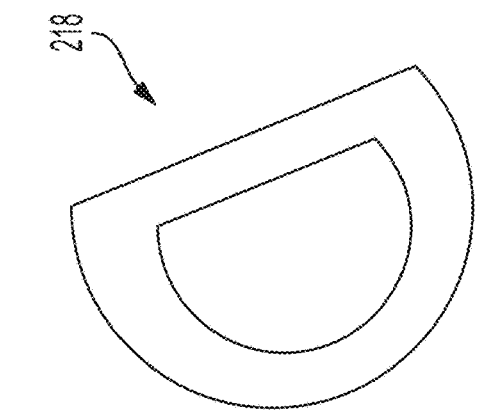
FIG. 21 is a top view of still another embodiment of a grommet.
Figure 20:
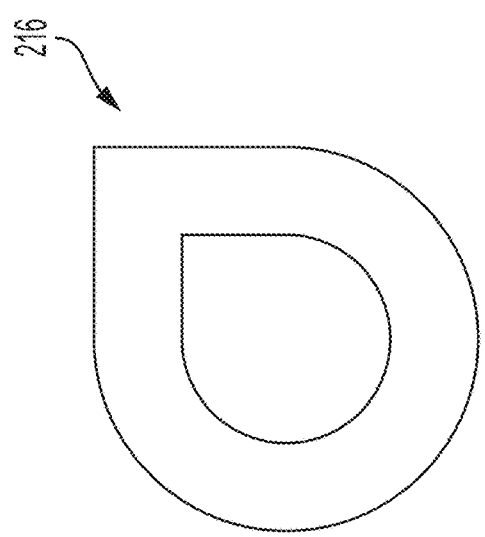
FIG. 20 is a top view of another embodiment of a grommet.

The grommet 200 is circular in the illustrated embodiment of FIGS. 15-17. The embodiments of grommets 208, 214, 222 illustrated in FIGS. 17-19 are also circular. A grommet can, however, have a shape other than circular. FIG. 20 illustrates another embodiment of a grommet 216 that has a teardrop shape. FIG. 21 illustrates another embodiment of a grommet 218 that has a D-shape.

Figure 22:
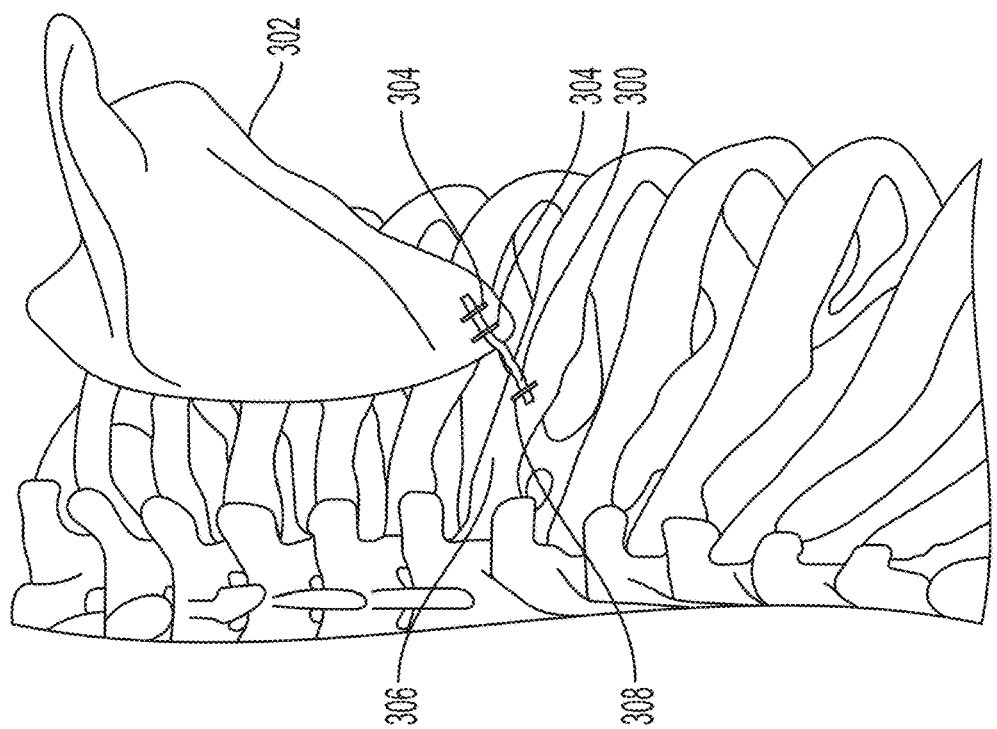
FIG. 22 is a rear view of another embodiment of a tether attached to a scapula and a rib.

FIG. 22 illustrates one embodiment in which a tether 300 is attached to a scapula 302 using at least one surgical staple 304 and to a rib 306 using at least one surgical staple 308. The tether 300 in this illustrated embodiment is attached to the scapula 302 using two surgical staples 304, but another number of surgical staples can be used. The tether 300 in this illustrated embodiment is attached to the rib 306 using one surgical staple 308, but another number of staples can be used. The surgical staples 304, 308 used to secure the tether 300 to the scapula 302 and the rib 306 are the same as one another in this illustrated embodiment, but any of the surgical staples 304, 308 can be different than any other of the surgical staples 304, 308. For example, differently sized surgical staples may be desirable to use at different bones and/or at different locations of the same bone. The tether 300 in this illustrated embodiment is a linear, non-looped flexible elongate member with a first terminal end of the tether 300 attached to the scapula 302 and a second terminal end of the tether 300 attached to the rib 306.

FIG. 22 illustrates the tether 300 attached to the scapula 302 and the rib 306 using the same type of attachment mechanism (surgical staples). Similarly, FIG. 17 illustrates the tether 206 attached to the scapula 202 and the rib 220 using the same type of attachment mechanism (grommets). In other embodiments, a tether can be attached to a scapula using one type of attachment mechanism (e.g., a grommet, a surgical staple, a suture anchor, etc.) and to a rib using another type of attachment mechanism.

As mentioned above, a tether can be attached to bone using a cam. The cam is configured to be implanted in a person and attached to bone of a person, e.g., a rib or a scapula. In some embodiments, a cam can be attached to a rib, a tether can be attached to the cam and thus be indirectly attached to the rib, and the tether can be attached to a scapula without using a cam. In some embodiments, a cam can be attached to a scapula, a tether can be attached to the cam and thus be indirectly attached to the scapula, and the tether can be attached to a rib without using a cam. In some embodiments, a first cam can be attached to a scapula, a tether can be attached to the first cam and thus be indirectly attached to the scapula, a second cam can be attached to a rib, and the tether can be attached to the second cam and thus be indirectly attached to the rib.

The cam can be attached to the bone in a variety of ways. For example, the cam can be adhered to the bone at an attachment point. For another example, the cam can include a protrusion, e.g., a peg, a spike, a screw, etc., configured to penetrate into the bone at the attachment point to secure the cam thereto.

The tether is configured to be attached to the cam, thereby indirectly attaching the tether to the bone. The tether attached to the cam extends along an exterior surface of the cam at least when the tether is in the elongated position. The tether can be attached to the cam in a variety of ways. For example, the tether can be directly attached to the cam such as by a terminal end of the tether as an elongate flexible member being attached to the cam, such as by being crimped by the cam, adhered to the cam, clipped to the cam, or attached to the cam using another attachment mechanism. For another example, the tether can be indirectly attached to the cam such as by a terminal end of the tether as an elongate flexible member being attached to the bone and positioned to wrap along the cam.

The cam is configured to move with a person's bone to which the cam is attached. The movement of the bone and the cam is relative to other bones of the person. For example, the movement of the person's scapula can cause a cam attached to the scapula to move relative to ribs of the person. The movement of the scapula also causes the tether to move, as discussed herein. The cam is configured to control a change in force applied to the scapula by the tether as the tether flexes and relaxes, e.g., as the tether changes in length. Controlling the change in force may better control the scapula's movement and thus improve treatment of scapular dyskinesis. The tether's attachment to the cam allows the movement of the cam to control the change in force applied to the scapula by the tether as the tether changes in length.

Figure 23:
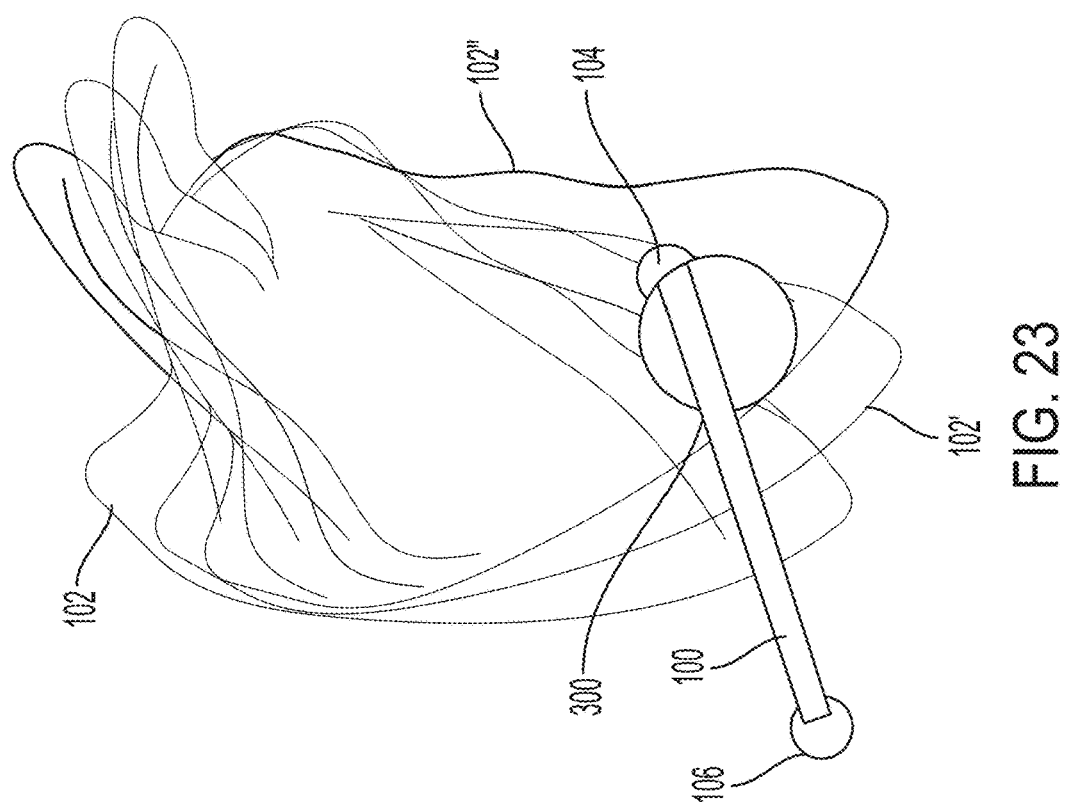
FIG. 23 is a rear view of scapular movement and the tether of FIG. 7 attached to the scapula using one embodiment of a cam.

FIG. 23 illustrates one embodiment of a cam 300 configured to be implanted in a person with the cam attached to bone of the person. The cam 300 in this illustrated embodiment is attached to the scapula 102 of FIG. 7. The tether 100 of FIG. 7 is attached to the cam 300 with the first terminal end 104 of the tether 100 being attached to the cam 300. The cam 300 is attached to the scapula 102 at the same first attachment point that the first terminal end 104 of the tether 100 is attached to the scapula 102 in FIG. 7. The second terminal end 106 of the tether 100 is attached to the rib at the same second attachment point as in FIG. 7.

FIG. 23 illustrates the same scapular motions as FIGS. 7-9 (and as FIGS. 11-13). With the scapula 102 in the normal resting position, the tether 100 has the first length L1 and the cam 300 is in an initial position. The tether 100 can have none of its length extending along an exterior surface of the cam 300 with the cam 300 in the initial position, or the tether 100 can have some of its length extending along the exterior surface of the cam 300 with the cam 300 in the initial position. With the scapula 102' in the first normal subsequent position, the tether 100 has the second length L2 and the cam 300 is in a first moved or subsequent position. The cam 300 in this illustrated embodiment moves counterclockwise with the scapula moving from the normal resting position (scapula labeled with reference numeral 102) to the first normal subsequent position (scapula labeled with reference numeral 102'). The tether 100 wraps along the cam's exterior surface as the cam 300 moves to move to the first moved position. The cam 300 can include a groove formed in the exterior surface configured to seat the tether 100 therein as the tether 100 wraps along the cam's exterior surface. The groove may help ensure that the tether 100 wraps predictably along the cam 300 (and unwraps predictably from the cam 300), which may help provide predictable forces to the scapula. With the scapula 102" in the second normal subsequent position, the tether 100 has the third length L3 and the cam 300 is in a second moved or subsequent position. The cam 300 moves further counterclockwise to move from the first moved position to the second moved position. The tether 100 wraps along the cam's exterior surface as the cam 300 moves to move to the second moved position. FIG. 23 shows the tether 100 in the second elongated position and the cam 300 in the second moved position. As the scapula 102" moves from the second normal subsequent position toward the normal resting position, the tether 100 unwraps from the cam's exterior surface as the cam 300 moves clockwise with the scapula.

Figure 24:
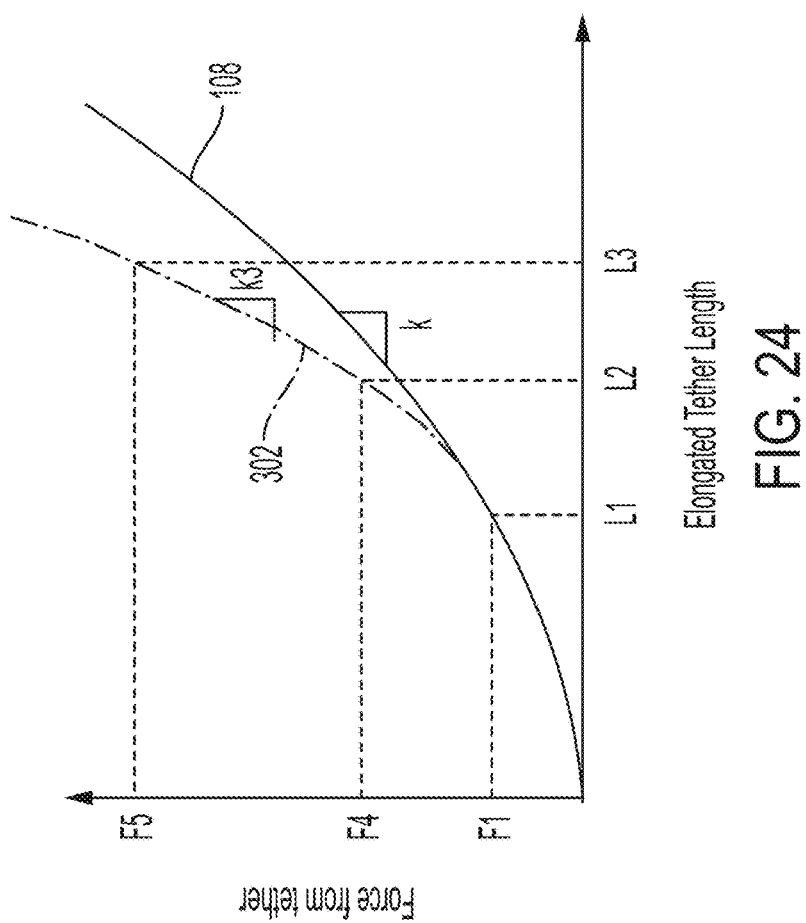
FIG. 24 is a graph showing force versus tether length for the tether of FIG. 23.

FIG. 24 illustrates with respect to FIG. 23 a graph of force from the tether 100 versus length of the tether 100. FIG. 24 demonstrates that the cam 300 is configured to control a change in force applied to the scapula by the tether 100 as the tether 100 changes in length. The graph of FIG. 24 is the same as the graph of FIG. 10 and the graph of FIG. 14 until a time after the tether 100 reaches the first length L1 and before the tether 100 reaches the second length L2. The tether 100 does not follow the curve 108 after this time due to the tether's interaction with the cam 300. The cam 300 prevents the tether 100 from following the curve 108 after this time, as the tether 100 wraps around the cam 300. The cam 300 thereby increases the effective stiffness of the tether 100 from its natural stiffness k to a greater stiffness k3, so higher forces are generated, as shown by a second curve 302 that the tether 100 follows after this time. The first force F1 in the graph of FIG. 24 corresponds to the force applied to the scapula 102 from the tether 100 with the scapula 102 in the normal resting position. A second force F4 in the graph of FIG. 24 corresponds to a force applied to the scapula 102 from the tether 100 with the scapula 102' in the first normal subsequent position. The second force F4 of FIG. 24 is greater than the second force F2 of FIGS. 10 and 14 even though a distance between the first and second attachment points is the same with or without the cam 300. The presence of the cam 300 and the interaction between the tether 100 and the cam 300 acts to increase the length of the tether 100 for this same change in scapular position, making the second force F4 with presence of the cam 300 greater than the second force F2 without presence of the cam 300. A third force F5 in the graph of FIG. 24 corresponds to a force applied to the scapula 102 from the tether 100 with the scapula 102" in the second normal subsequent position. The third force F5 of FIG. 24 is greater than the third force F3 of FIGS. 10 and 14 even though the distance between the first and second attachment points is the same with or without the cam 300. The presence of the cam 300 and the interaction between the tether 100 and the cam 300 acts to increase the length of the tether 100 for this same change in scapular position, making the third force F5 with presence of the cam 300 greater than the third force F3 without presence of the cam 300.

Figure 25:
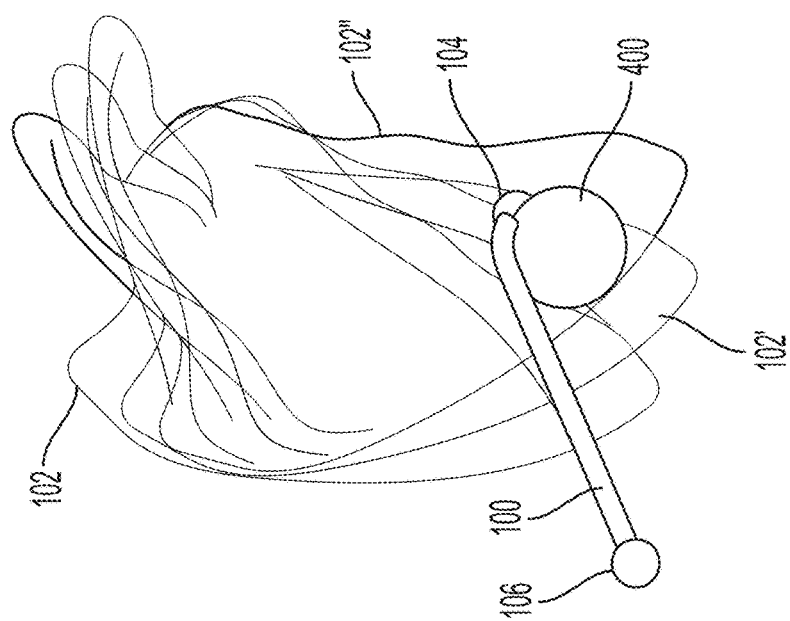
FIG. 25 is a rear view of scapular movement and the tether of FIG. 7 attached to the scapula using another embodiment of a cam.

FIG. 25 illustrates another embodiment of a cam 400 configured to be implanted in a person and attached to bone of a person. The cam 400 in this illustrated embodiment is attached to the scapula 102 of FIG. 7. The tether 100 of FIG. 7 is attached to the cam 400 with the first terminal end 104 of the tether 100 being attached to the cam 400. The cam 400 is attached to the scapula 102 at the same first attachment point that the first terminal end 104 of the tether 100 is attached to the scapula 102 in FIG. 7. The second terminal end 106 of the tether 100 is attached to the rib at the same second attachment point as in FIG. 7.

FIG. 25 illustrates the same scapular motions as FIGS. 7-9 (and as FIGS. 11-13 and 23). With the scapula 102 in the normal resting position, the tether 100 has the first length L1 and the cam 400 is in an initial position. The tether 100 has a length extending along an exterior surface of the cam 400 with the cam 400 in the initial position. The cam 400 can include a groove formed in the exterior surface configured to seat the tether 100. The groove may help ensure that the tether 100 unwraps predictably from the cam 400 (and wraps predictably along the cam 400), which may help provide predictable forces to the scapula. With the scapula 102' in the first normal subsequent position, the tether 100 has the second length L2 and the cam 400 is in a first moved position. The cam 400 in this illustrated embodiment moves clockwise with the scapula moving from the normal resting position (scapula labeled with reference numeral 102) to the first normal subsequent position (scapula labeled with reference numeral 102'). The tether 100 unwraps from along the cam's exterior surface as the cam 400 moves to the first rotated position. With the scapula 102" in the second normal subsequent position, the tether 100 has the third length L3 and the cam 400 is in a second moved position. The cam 400 moves clockwise to move from the first moved position to the second moved position. The tether 100 unwraps from the cam's exterior surface as the cam 400 moves to the second moved position. FIG. 24 shows the tether 100 in the second elongated position and the cam 400 in the second moved position. As the scapula 102" moves from the second normal subsequent position toward the normal resting position, the tether 100 wraps along the cam's exterior surface as the cam 400 moves with the scapula.

Figure 26:
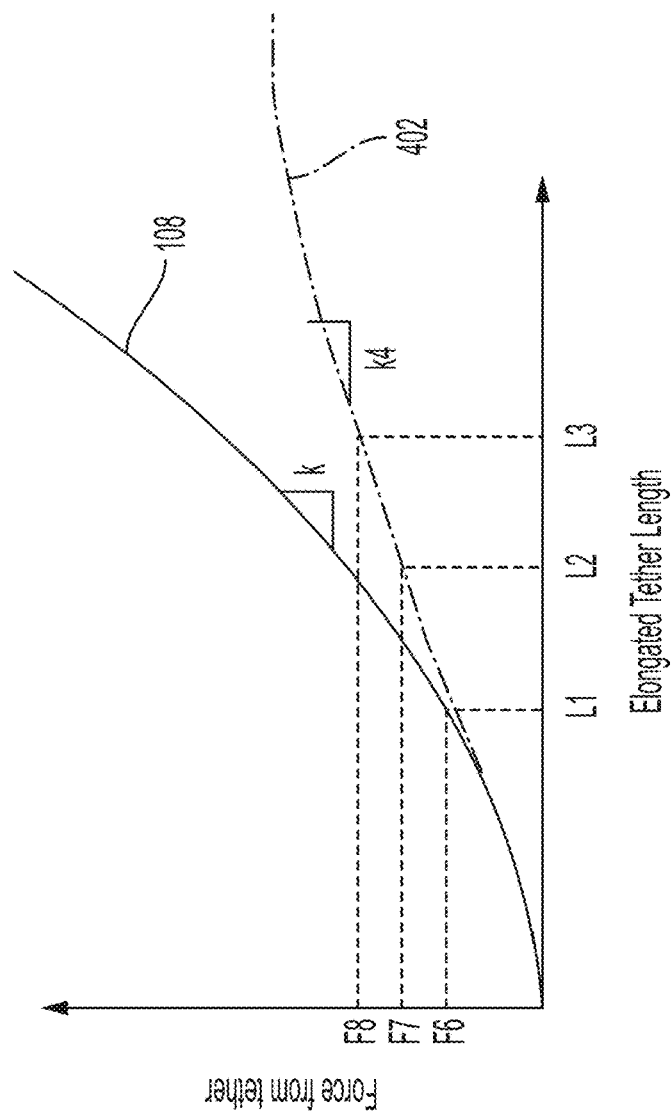
FIG. 26 is a graph showing force versus tether length for the tether of FIG. 25.

FIG. 26 illustrates with respect to FIG. 25 a graph of force from the tether 100 versus length of the tether 100. FIG. 26 demonstrates that the cam 400 is configured to control a change in force applied to the scapula by the tether 100 as the tether 100 flexes, e.g., as the tether 100 changes in longitudinal length. The graph of FIG. 26 is the same as the graph of FIG. 10 and the graph of FIG. 14 until a time before the tether 100 reaches the first length L1. The tether 100 does not follow the curve 108 after this time. The cam 400 prevents the tether 100 from following the curve 108 after this time, as the tether 100 unwraps from around the cam 400. The cam 400 decreases the effective stiffness of the tether 100 from its natural stiffness k to a lesser stiffness k4, so lower forces are generated, as shown by a second curve 402 that the tether 100 follows after this time. A first force F6 in the graph of FIG. 26 corresponds to the force applied to the scapula 102 from the tether 100 with the scapula 102 in the normal resting position. The first force F6 of FIG. 26 is less than the first force F1 of FIGS. 10, 14, and 24 even though a distance between the first and second attachment points is the same with or without the cam 400. A second force F7 in the graph of FIG. 26 corresponds to a force applied to the scapula 102 from the tether 100 with the scapula 102' in the first normal subsequent position. The second force F7 of FIG. 26 is less than the second force F2 of FIGS. 10 and 14 and the second force F4 of FIG. 24 even though the distance between the first and second attachment points is the same with or without the cam 400. A third force F8 in the graph of FIG. 26 corresponds to a force applied to the scapula 102 from the tether 100 with the scapula 102" in the second normal subsequent position. The third force F8 of FIG. 26 is less than the third force F3 of FIGS. 10 and 14 and the third force F5 of FIG. 24 even though the distance between the first and second attachment points is the same with or without the cam 400. The unwrapping of the tether 100 in this illustrated embodiment with motion of the scapula from the initial normal position (or other normal position) toward the second normal subsequent position allows the force exerted by the tether 100 on the scapula to be lower as compared the wrapping of the tether 100 with motion of the scapula from the initial normal position (or other normal position) toward the second normal subsequent position.

The tether 100 of FIGS. 23 and 25 is attached to an exterior surfaces of the cams 300, 400 and is located entirely outside of the cams 300, 400 (although a nominal portion of the tether 100 may be located inside the cams 300, 400 for tether attachment purposes). In other embodiments, a tether can extend through an interior of a cam. The tether extending through the interior of the cam allows for an abrupt change in the tether's effective stiffness when the tether moves from an initial position and interacts with the cam. The abrupt change is an increase in the tether's effective stiffness.

Figure 27:
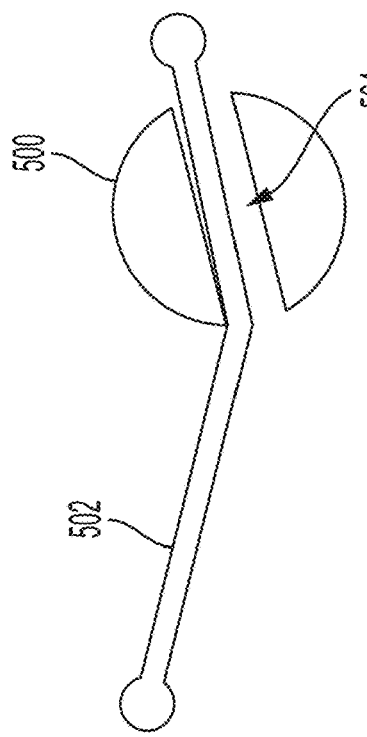
FIG. 27 is a cross-sectional view of another embodiment of a tether and another embodiment of a cam.
Figure 28:
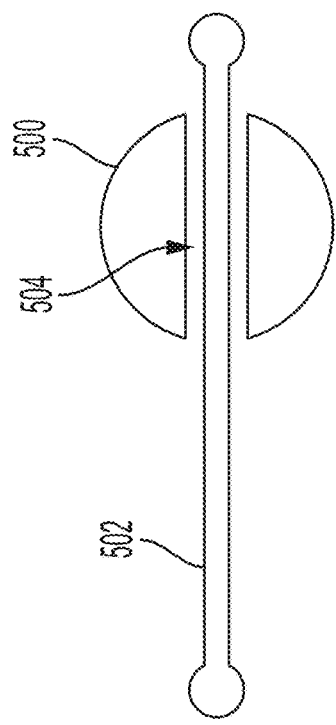
FIG. 28 is a cross-sectional view of the tether and the cam of FIG. 27 with the cam moved from its position in FIG. 27.

FIGS. 27 and 28 illustrate one embodiment of a cam 500 configured to attach to a tether 502 with the tether 502 extending through an interior of the cam 500. An inner passageway 504 extends through the cam 500, and the tether 502 extends through the inner passageway 504. The inner passageway 504 is an enclosed tunnel or slot extending through the cam 500. The inner passageway 504 is centrally located in the cam 500 in this illustrated embodiment but can instead be located non-centrally. FIG. 27 shows the cam 500 in an initial position and the tether 502 in an initial position. FIG. 28 shows the cam in a moved position and the tether 502 in an elongated position. The cam 500 is configured to move counterclockwise in this illustrated embodiment to move from the initial position to the moved position with motion of the scapula from its initial position. When the cam 500 begins to move from the initial position and the tether 502 impinges on a side of the inner passageway 504, as shown in FIG. 28, the tether's effective stiffness abruptly increases for further cam movement in the same direction (counterclockwise in this illustrated embodiment).

The cams 300, 400, 500 of FIGS. 23, 25, 27, and 28 have circular cross-sections. A cam can have another cross sectional shape, e.g., teardrop-shaped, hexagonal, pentagonal, octagonal, square, etc. For cross-sectional shapes with corners around which the tether can wrap and unwrap, the tether wrapping around a corner causes an abrupt change (e.g., increase) in the tether's effective stiffness, and the tether unwrapping from around a corner also causes an abrupt change (e.g., decrease) in the tether's effective stiffness.

Figure 29:
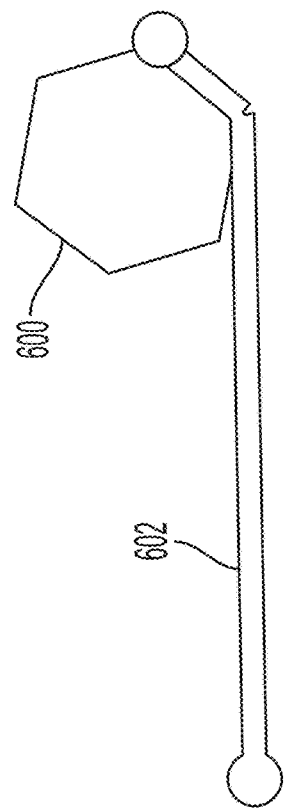
FIG. 29 is a cross-sectional view of another embodiment of a tether and another embodiment of a cam.
Figure 30:
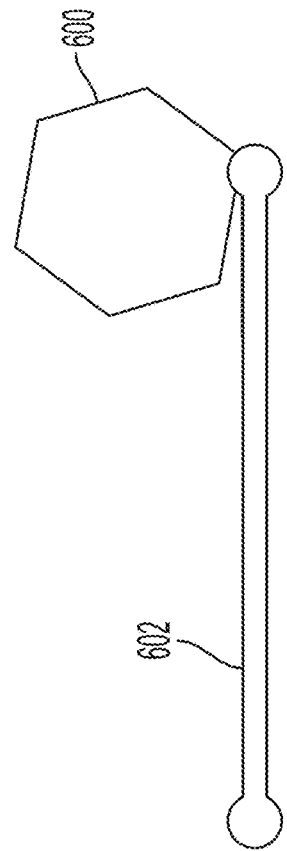
FIG. 30 is a cross-sectional view of the tether and the cam of FIG. 29 with the cam moved from its position in FIG. 29.

FIGS. 29 and 30 illustrate one embodiment of a cam 600 having a non-circular cross-sectional shape. The non-circular cross-sectional shape is hexagonal in this illustrated embodiment. The cam 600 is configured to attach to a tether 602 with the tether 602 attached to an exterior surface of the cam 600. A cam with a non-circular cross-sectional shape can, however, be attachable to a tether with the tether extending through an interior of the cam. When the cam 600 begins to move from the initial position and the tether 602 wraps around a corner of the cam 600, as shown in FIG. 30, the tether's effective stiffness abruptly increases for further cam movement in the same direction (counterclockwise in this illustrated embodiment).

Figure 31:
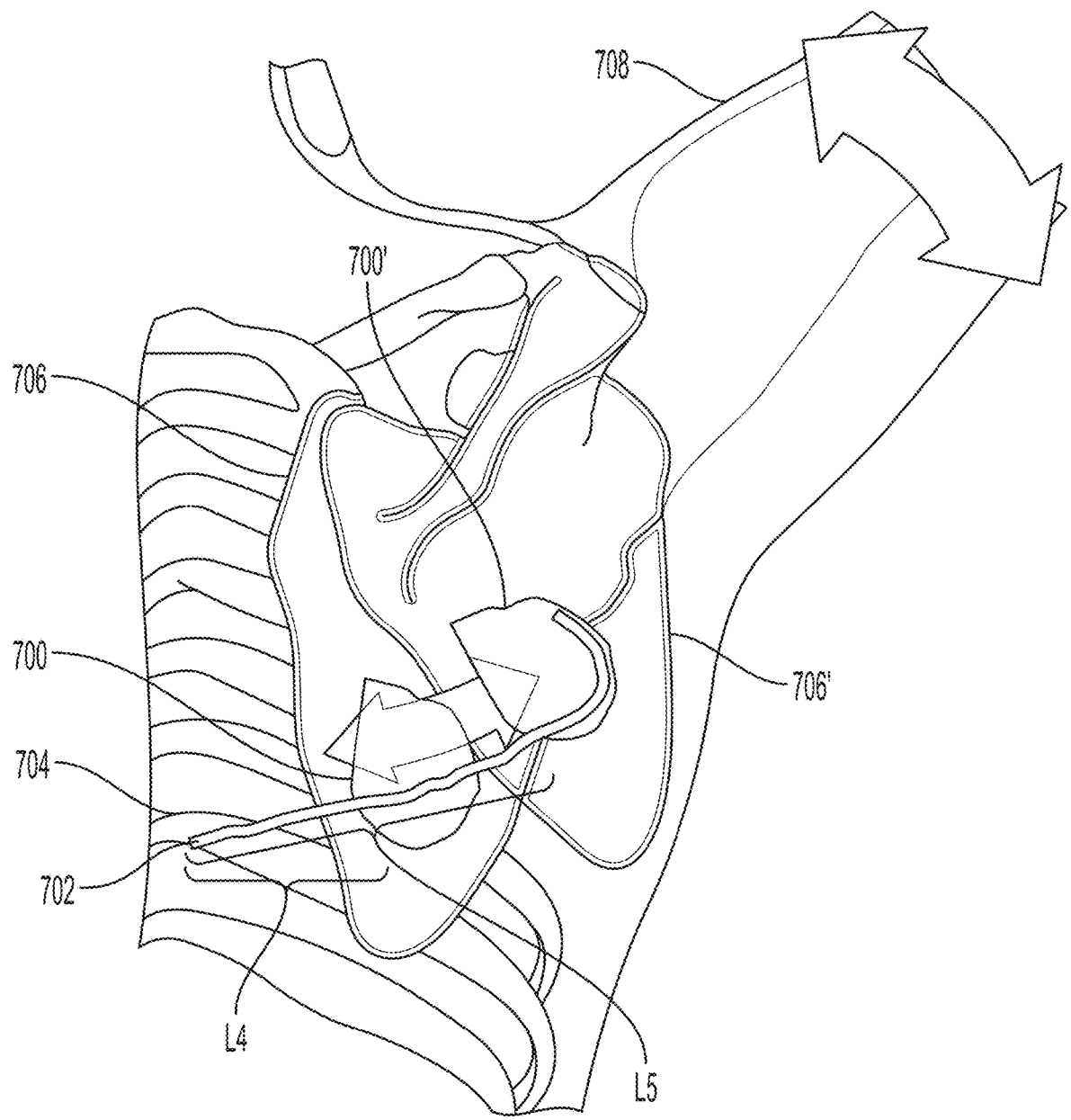
FIG. 31 is a rear view of scapular motion and another embodiment of a cam attached to a scapula and another embodiment of a tether attached to the scapula and to a rib.

FIG. 31 illustrates another embodiment of a cam 700 having a non-circular cross-sectional shape. The non-circular cross-sectional shape is teardrop-shaped in this illustrated embodiment. The cam 700 in this illustrated embodiment is attached to a tether 702 with the tether 702 extending along an exterior surface of the cam 700. The tether 702 in this illustrated embodiment is attached to a rib 704, and the cam 700 in this illustrated embodiment is attached to a scapula 706. FIG. 31 illustrates movement of the scapula 706 from a normal resting position (scapula labeled with reference numeral 706) to a normal subsequent position (scapula labeled with reference numeral 706') accompanying motion of the person's arm 708. As the scapula moves from the normal resting position to the normal subsequent position, the cam 700 moves (counterclockwise in this illustrated embodiment) and the tether 702 wraps along the exterior surface of the cam 700. The exterior surface of the cam 700 can have a groove formed therein that is configured to seat the tether 702 therein as the tether 702 wraps along the cam's exterior surface.

Figure 32:
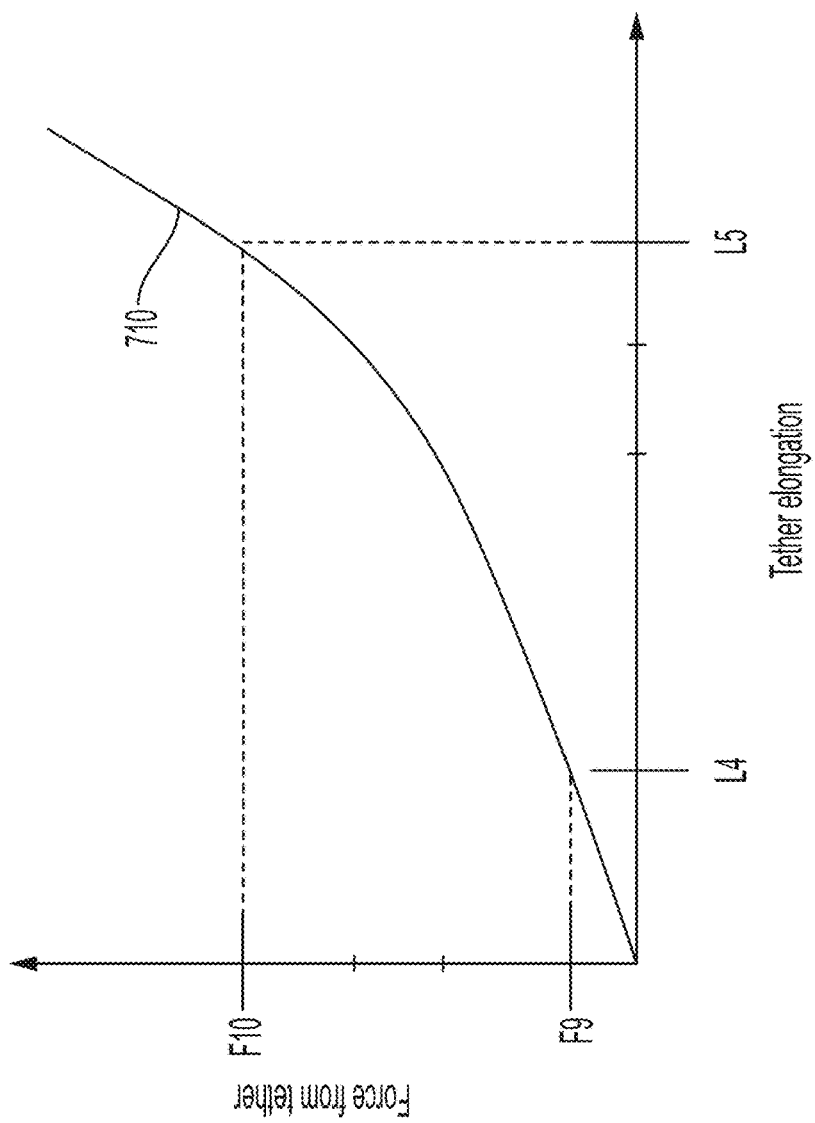
FIG. 32 is a graph showing force versus tether length for the tether of FIG. 31.

FIG. 32 illustrates with respect to FIG. 31 a graph of force from the tether 702 versus length of the tether 702. FIG. 32 demonstrates that the cam 700 is configured to control a change in force applied to the scapula by the tether 702 as the tether 702 changes in length. A curve 710 in the graph shows a force-elongation relationship for the tether 702. A first force F9 in the graph of FIG. 32 corresponds to a force applied to the scapula from the tether 702 with the scapula 706 in the normal resting position. A second force F10 in the graph of FIG. 32 corresponds to a force applied to the scapula from the tether 702 with the scapula 706' in the first normal subsequent position. As shown in the graph, the more elongated the tether 702, the greater the force exerted by the tether 702 on the scapula.

By using a cam with a different diameter than a diameter of the cam 700 to which the tether 702 is attached, the force-elongation relationship curve will change. A cam can be chosen according to a particular desired scapular motion.

The tethers 14, 18, 20, 100, 206, 300, 502, 602, 702 in the illustrated embodiments of FIGS. 4, 5, 7-9, 11-13, 16, 17, 22, 23, 25, and 27-31 each include an elongate flexible member. In some embodiments, a plurality of elongate flexible members can be provided in series to define the tether. Each of the plurality of elongate flexible members can be the same as each other or different from at least one other of the elongate flexible members. A tether can have configurations other than an elongate flexible member, such as a planar flexible member in the form of a mesh or a scaffold.

The latissimus dorsi muscle is a muscle on a person's back that is attached to the spine and can influence movement of the scapula. In normal circumstances, the latissimus dorsi muscle covers an inferior tip of the scapula throughout scapular motion. However, in some instances, the latissimus dorsi muscle does not adequately cover the inferior tip of the scapula throughout scapular motion. In such instances, when a person raises an arm, the tip of the scapula can rotate superiorly above coverage of the latissimus dorsi muscle, wing dorsally, and sometimes become entrapped superficially. The lack of coverage is most pronounced when the arm is fully raised.

A tether including a planar flexible member implanted in a person's body can be configured to build up the latissimus dorsi muscle superiorly and thereby affect scapula motion. The planar flexible member can be implanted in the body with the planar flexible member attached to a single muscle, e.g., the latissimus dorsi muscle. Alternatively, the flexible member can be implanted in the body with the planar flexible member attached to a first muscle, e.g., the latissimus dorsi muscle, and to a second, different muscle. The planar flexible member can be attached to the muscle(s) in any of a variety of ways, such as by using at least one suture or using another soft tissue approximation technique. The planar flexible member being attached to one or two muscles allows the planar flexible member to build up the latissimus dorsi muscle superiorly. The primary motion restricted by the planar flexible member so implanted is dorsal motion.

Figure 33:
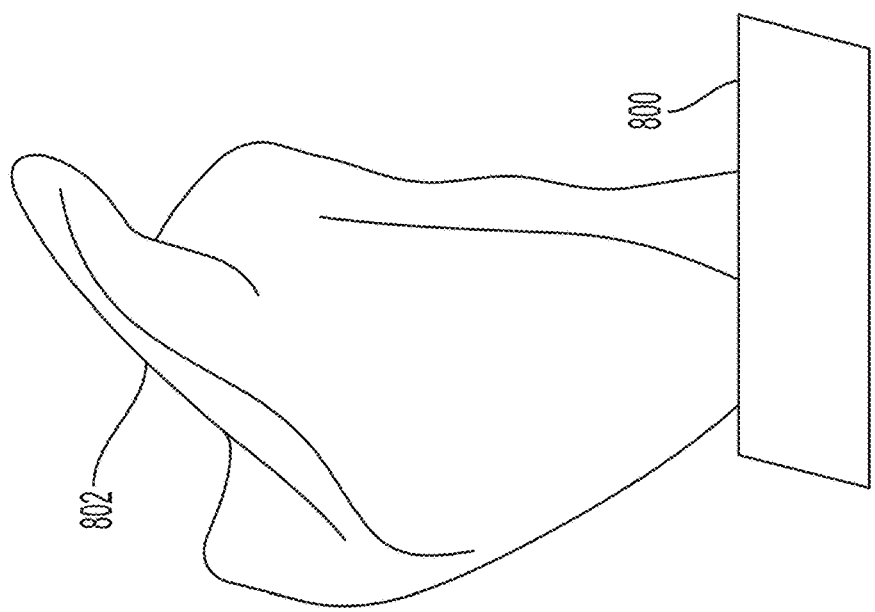
FIG. 33 is a rear view of a right scapula attached to another embodiment of a tether.

FIG. 33 illustrates one embodiment of a tether including a planar flexible member 800 implanted in a body of a person. The planar flexible member 800 is implanted superior to an inferior tip of a scapula 802 in this illustrated embodiment.

In some embodiments, at least one flexible member and at least one substantially rigid member can be provided in series to define the tether. The at least one flexible member can be configured as any of the flexible member embodiments discussed herein. In some embodiments, the at least one flexible member includes a mechanical spring, such as a coil spring, a volute spring, etc. The substantially rigid member can be formed of any of a variety of materials, such as stainless steel, a shape memory material (e.g., Nitinol, etc.), etc. Unlike the substantially rigid elongate member as position limiter discussed above, the at least one substantially rigid member defining a portion of the tether is not configured to move between a slackened configuration and a taut configuration. The at least one substantially rigid member defining a portion of the tether is configured to dampen linear motion of the tether and to ensure that the tether has a minimum length, regardless of whether the at least one flexible member of the tether is in the relaxed position or the flexed position, since the at least one substantially rigid member does not change in length due to its substantial rigidity.

In some embodiments, at least one flexible member and a trimming potentiometer (also referred to as a "trim pot") can be provided in series to define the tether. The at least one flexible member can be configured as any of the flexible member embodiments discussed herein. In some embodiments, the at least one flexible member includes a mechanical spring, such as a coil spring, a volute spring, etc. The trim pot defining a portion of the tether is configured to dampen linear motion of the tether and to help alter the elastic characteristics of the tether.

Regardless of whether the tether includes an elongate flexible member or a planar flexible member, in an exemplary embodiment, the tether is resorbable. A surgical procedure thus need not be performed to remove the tether. The tether, before being bioabsorbed by the person's body, is configured to train the person's muscles to move in a certain way that corresponds to normal scapular movement. Thus, after the tether has been bioabsorbed, the muscles move for normal scapular movement.

Regardless of whether the tether includes an elongate flexible member or a planar flexible member, the tether can be configured to release a medicant therefrom, such as a medicant configured to promote muscle growth. Examples of medicants configured to promote muscle growth include anabolic-androgenic steroids, such as naturally-occurring testosterone and androstane. Various embodiments of medicants and various embodiments of structures and materials configured to release a medicant therefrom are further described in U.S. Pat. No. 10,569,071 entitled "Medicant Eluting Adjuncts And Methods Of Using Medicant Eluting Adjuncts" issued Feb. 25, 2020, which is hereby incorporated by reference in its entirety.

In some embodiments, instead of using a tether to limit scapular motion, a plurality of magnets can be used to affect scapular motion. The magnets' effect on scapular motion can be to enhance scapulothoracic motion, whereas the tethers discussed are configured to restrict scapulothoracic motion. For example, the plurality of magnets can be configured to help a person raise their arm over their head by helping to overcome the force of gravity.

The plurality of magnets are configured to be implanted in, such as by being embedded in, at least two bones of a person and to repel or attract the bones depending on a position of the person's arm, e.g., depending on movement of the person's scapula. The orientation of the magnets' poles relative to each other is configured to provide the repelling and attracting to limit the scapula motion. In an exemplary embodiment, at least one magnet is implanted in a scapula of the person and at least one magnet is implanted in a rib of the patient. The at least one magnet implanted in the scapula is configured to repel or attract the at least one magnet implanted in the at least one rib such that the scapula repels or attracts the at least one rib. A north pole of each of the one or magnets implanted in the rib(s) can face superficially, and the one or more magnets implanted in the scapula can have poles similarly oriented such that the one or more magnets implanted in the scapula are located directly on top of the one or more magnets implanted in the rib(s) when the person's arm is fully elevated to allow attraction of the scapula magnet(s) and rib magnet(s). This attraction of the magnets may help the person raise their arm over their head by driving motion between the scapula and the rib(s) with the magnet(s) to their closest approximation. In embodiments including at least three magnets, at least one of the magnets can be implanted in the scapula and a remainder of the magnets can be implanted in the rib, either the same rib or two or more different ribs.

One skilled in the art will appreciate further features and advantages of the devices, systems, and methods based on the above-described embodiments. Accordingly, this disclosure is not to be limited by what has been particularly shown and described, except as indicated by the appended claims. All publications and references cited herein are expressly incorporated herein by reference in their entirety.

The present disclosure has been described above by way of example only within the context of the overall disclosure provided herein. It will be appreciated that modifications within the spirit and scope of the claims may be made without departing from the overall scope of the present disclosure.

What is claimed is:

1. A surgical method, comprising:
    attaching a first terminal end of a flexible implant to a first body structure of a person; and
    attaching a second terminal end of the flexible implant to a second body structure of the person;
    wherein the flexible implant, with the first and second terminal ends attached, is configured to affect motion of a scapula of the person with respect to a thorax of the person; and
    wherein the first body structure is a rib of a person, and the second body structure is the scapula of the person.

2. The method of claim 1, wherein the flexible implant, with the first and second terminal ends attached, is configured to change in length in response to movement of the scapula of the person accompanying arm movement of the person, the change in length of the flexible implant changing a force applied by the flexible implant to the scapula.

3. The method of claim 1, further comprising attaching a third terminal end of a second flexible implant to the person; and
    attaching a fourth terminal end of the second flexible implant to the scapula of the person.

4. The method of claim 3, further comprising attaching a cam to the scapula of the person, the cam being configured to move with the scapula, and the flexible implant extending along an exterior surface of the cam during the movement of the scapula.

5. The method of claim 3, wherein attaching the third terminal end includes attaching the third terminal end of the second flexible implant directly to the rib of the person.

6. The method of claim 3, wherein attaching the third terminal end includes attaching the third terminal end of the second flexible implant indirectly to the rib of the person using a grommet attached to the rib of the person.

7. The method of claim 1, wherein attaching the first terminal end includes attaching the first terminal end of the flexible implant directly to the rib of the person.

8. The method of claim 1, wherein attaching the first terminal end includes attaching the first terminal end of the flexible implant indirectly to the rib of the person using a grommet attached to the rib of the person.

9. The method of claim 1, wherein attaching the second terminal end includes attaching the second terminal end of the flexible implant directly to the scapula of the person.

10. The method of claim 1, further comprising attaching a cam to the scapula of the person;
    wherein the cam moves with the scapula, and the flexible implant extends along an exterior surface of the cam; and
    wherein attaching the second terminal end includes attaching the second terminal end of the flexible implant indirectly to the scapula of the person via the second terminal end being attached to the cam.

11. The method of claim 10, wherein the cam moves in a first direction, and the flexible implant increases in length, with the movement of the scapula; and
    after the movement of the cam in the first direction, the cam is configured to move in a second, opposite direction with movement of the scapula accompanying another arm movement of the person, the flexible implant decreasing in length simultaneously with the movement of the cam in the second direction.

12. The method of claim 1, further comprising attaching a cam to the rib of the person;
    wherein the flexible implant extends along an exterior surface of the cam during the movement of the scapula.

13. The method of claim 1, wherein attaching the second terminal end to the scapula includes attaching the second terminal end to an inferior tip of the scapula.

\* \* \* \* \*